United States Patent
Francois et al.

(10) Patent No.: US 10,646,321 B2
(45) Date of Patent: May 12, 2020

(54) PROSTHESIS FOR HERNIA REPAIR

(71) Applicant: Sofradim Production, Trévoux (FR)

(72) Inventors: Sebastien Francois, Rhone (FR); Michel Therin, Hauts-de-Seine (FR); Nicolas Prost, Rhone (FR)

(73) Assignee: Sofradim Production, Trévoux (FR)

( * ) Notice: Subject to any disclaimer, the term of this patent is extended or adjusted under 35 U.S.C. 154(b) by 410 days.

(21) Appl. No.: 15/384,435

(22) Filed: Dec. 20, 2016

(65) Prior Publication Data

US 2017/0209251 A1 Jul. 27, 2017

(30) Foreign Application Priority Data

Jan. 25, 2016 (EP) .................................... 16305063

(51) Int. Cl.
*A61F 2/00* (2006.01)

(52) U.S. Cl.
CPC ...... *A61F 2/0063* (2013.01); *A61F 2002/009* (2013.01); *A61F 2002/0068* (2013.01); *A61F 2210/0076* (2013.01); *A61F 2220/0058* (2013.01); *A61F 2230/0019* (2013.01); *A61F 2240/00* (2013.01); *A61F 2250/0051* (2013.01)

(58) Field of Classification Search
CPC .............. A61F 2/0063; A61F 2002/009; A61F 2210/0076; A61F 2250/0051; A61F 2230/0019; A61F 2220/0058; A61F 2002/0068; A61F 2240/00
See application file for complete search history.

(56) References Cited

U.S. PATENT DOCUMENTS

| | | |
|---|---|---|
| 1,187,158 A | 6/1916 | Mcginley |
| 3,054,406 A | 9/1962 | Usher |
| 3,118,294 A | 1/1964 | Van Laethem |
| 3,124,136 A | 3/1964 | Usher |
| 3,272,204 A | 9/1966 | Charles et al. |
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 3,718,725 A | 2/1973 | Hamano |
| 4,006,747 A | 2/1977 | Kronenthal et al. |
| 4,060,081 A | 11/1977 | Yannas et al. |

(Continued)

FOREIGN PATENT DOCUMENTS

| | | |
|---|---|---|
| CA | 1317836 C | 5/1993 |
| CN | 201879864 U | 6/2011 |

(Continued)

OTHER PUBLICATIONS

Malette, W. G. et al., "Chitosan, A New Hemostatic," Ann Th. Surg., Jul. 1983, pp. 55-58, 36.

(Continued)

*Primary Examiner* — Kaylee R Wilson

(57) ABSTRACT

The present invention relates to a prosthesis (1) for hernia repair comprising a reinforcement layer (2), a first barrier layer (3) of anti-adhesion material covering at least a part of a surface of the reinforcement layer, and a second barrier layer of anti-adhesion material covering a remaining part of the surface of the reinforcement layer, the second barrier layer being formed of one or more flap member(s) (4).

21 Claims, 6 Drawing Sheets

(56) References Cited

U.S. PATENT DOCUMENTS

| | | |
|---|---|---|
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 4,976,737 A | 12/1990 | Leake |
| 5,002,551 A | 3/1991 | Linsky et al. |
| 5,015,584 A | 5/1991 | Brysk |
| 5,116,357 A | 5/1992 | Eberbach |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,195,542 A | 3/1993 | Gazielly et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,258,000 A | 11/1993 | Gianturco |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,368,602 A | 11/1994 | de la Torre |
| 5,370,650 A | 12/1994 | Tovey et al. |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,676,967 A | 10/1997 | Williams et al. |
| 5,681,568 A | 10/1997 | Goldin et al. |
| 5,686,090 A | 11/1997 | Schilder et al. |
| 5,686,115 A | 11/1997 | Voumakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,702,416 A | 12/1997 | Kieturakis et al. |
| 5,709,934 A | 1/1998 | Bell et al. |
| 5,711,960 A | 1/1998 | Shikinami |
| 5,716,409 A | 2/1998 | Debbas |
| 5,720,981 A | 2/1998 | Eisinger |
| 5,732,572 A | 3/1998 | Litton |
| 5,743,917 A | 4/1998 | Saxon |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |
| 6,042,534 A | 3/2000 | Gellman et al. |
| 6,042,592 A | 3/2000 | Schmitt |
| 6,043,089 A | 3/2000 | Sugiyama et al. |

(56) References Cited

U.S. PATENT DOCUMENTS

| | | |
|---|---|---|
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,090,116 A | 7/2000 | D'Aversa et al. |
| 6,113,623 A | 9/2000 | Sgro |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,162,962 A | 12/2000 | Hinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,180,848 B1 | 1/2001 | Flament et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,306,424 B1 | 10/2001 | Vyakamam et al. |
| 6,312,474 B1 | 11/2001 | Francis et al. |
| 6,319,264 B1 | 11/2001 | Tormala et al. |
| 6,328,686 B1 | 12/2001 | Kovac |
| 6,334,872 B1 | 1/2002 | Termin et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Muller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,670,018 B2 | 12/2003 | Fujita et al. |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Cornwall et al. |
| 6,723,335 B1 | 4/2004 | Moehlenbruck et al. |
| 6,726,660 B2 | 4/2004 | Hessel et al. |
| 6,730,299 B1 | 5/2004 | Tayot et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,743,435 B2 | 6/2004 | DeVore et al. |
| 6,746,458 B1 | 6/2004 | Cloud |
| 6,752,834 B2 | 6/2004 | Geistlich et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr, Jr. et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |

(56) References Cited

U.S. PATENT DOCUMENTS

| | | |
|---|---|---|
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,380 B2 | 3/2010 | Cauthen, III |
| 7,682,381 B2 | 3/2010 | Rakos et al. |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,900,484 B2 | 3/2011 | Cherok et al. |
| 7,931,695 B2 | 4/2011 | Ringeisen |
| 8,052,759 B2 | 11/2011 | Dupic et al. |
| 8,079,023 B2 | 12/2011 | Chen |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,435,307 B2 | 5/2013 | Paul |
| 8,470,355 B2 | 6/2013 | Skalla et al. |
| 8,562,633 B2 | 10/2013 | Cully et al. |
| 8,574,627 B2 | 11/2013 | Martakos et al. |
| 8,709,094 B2 | 4/2014 | Stad et al. |
| 8,734,471 B2 | 5/2014 | Deitch |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,911,504 B2 | 12/2014 | Mathisen et al. |
| 8,920,370 B2 | 12/2014 | Sholev et al. |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 9,034,357 B2 | 5/2015 | Stopek |
| 9,113,993 B2 | 8/2015 | Lee |
| 9,211,175 B2 | 12/2015 | Stopek et al. |
| 9,216,075 B2 | 12/2015 | Bailly et al. |
| 2002/0087174 A1 | 7/2002 | Cabello |
| 2002/0095218 A1 | 7/2002 | Carr et al. |
| 2003/0086975 A1 | 5/2003 | Ringeisen |
| 2003/0106346 A1 | 6/2003 | Matsumoto |
| 2003/0114937 A1 | 6/2003 | Leatherbury et al. |
| 2003/0133967 A1 | 7/2003 | Ruszczak et al. |
| 2003/0212462 A1 | 11/2003 | Gryska et al. |
| 2003/0225355 A1 | 12/2003 | Butler |
| 2004/0019360 A1* | 1/2004 | Farnsworth ........... A61F 2/0063 606/151 |
| 2004/0034373 A1 | 2/2004 | Schuldt-Hempe et al. |
| 2004/0054376 A1 | 3/2004 | Ory et al. |
| 2004/0059356 A1 | 3/2004 | Gingras |
| 2004/0101546 A1 | 5/2004 | Gorman et al. |
| 2004/0215219 A1* | 10/2004 | Eldridge ............... A61F 2/0063 606/151 |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0015143 A1* | 1/2006 | Alvarado ............... A61F 2/0063 606/213 |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0088391 A1 | 4/2007 | McAlexander et al. |
| 2007/0129736 A1 | 6/2007 | Solecki |
| 2007/0198040 A1 | 8/2007 | Buevich et al. |
| 2007/0299538 A1 | 12/2007 | Roeber |
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0172071 A1 | 7/2008 | Barker |
| 2008/0255593 A1 | 10/2008 | St-Germain |
| 2009/0035341 A1 | 2/2009 | Wagener et al. |
| 2009/0036996 A1 | 2/2009 | Roeber |
| 2009/0068250 A1 | 3/2009 | Gravagna et al. |
| 2009/0105526 A1 | 4/2009 | Piroli Torelli et al. |
| 2009/0163936 A1 | 6/2009 | Yang et al. |
| 2009/0187197 A1 | 7/2009 | Roeber et al. |
| 2009/0192530 A1 | 7/2009 | Adzich et al. |
| 2009/0204129 A1 | 8/2009 | Fronio |
| 2009/0216338 A1 | 8/2009 | Gingras et al. |
| 2009/0270999 A1 | 10/2009 | Brown |
| 2009/0281558 A1 | 11/2009 | Li |
| 2009/0318752 A1 | 12/2009 | Evans et al. |
| 2010/0104608 A1 | 4/2010 | Abuzaina et al. |
| 2010/0318108 A1 | 12/2010 | Datta et al. |
| 2011/0015760 A1 | 1/2011 | Kullas |
| 2011/0144667 A1 | 6/2011 | Horton et al. |
| 2011/0190795 A1 | 8/2011 | Hotter et al. |
| 2011/0238094 A1 | 9/2011 | Thomas et al. |
| 2011/0251699 A1 | 10/2011 | Ladet |
| 2011/0257666 A1 | 10/2011 | Ladet et al. |
| 2012/0016388 A1 | 1/2012 | Houard et al. |
| 2012/0029537 A1 | 2/2012 | Mortarino |
| 2012/0065727 A1 | 3/2012 | Reneker et al. |
| 2012/0082712 A1 | 4/2012 | Stopek et al. |
| 2012/0116425 A1 | 5/2012 | Intoccia et al. |
| 2012/0150204 A1 | 6/2012 | Mortarino et al. |
| 2012/0165937 A1 | 6/2012 | Montanari et al. |
| 2012/0179175 A1 | 7/2012 | Hammell |
| 2012/0179176 A1 | 7/2012 | Wilson et al. |
| 2012/0197415 A1 | 8/2012 | Montanari et al. |
| 2013/0317527 A1* | 11/2013 | Jacinto ............... A61B 17/0057 606/151 |
| 2014/0044861 A1 | 2/2014 | Boey et al. |

(56) References Cited

U.S. PATENT DOCUMENTS

| | | | |
|---|---|---|---|
| 2014/0364684 A1 | 12/2014 | Lecuivre | |
| 2015/0094743 A1* | 4/2015 | Russo | A61F 2/0063 606/151 |

FOREIGN PATENT DOCUMENTS

| | | |
|---|---|---|
| DE | 19544162 C1 | 4/1997 |
| DE | 19718903 A1 | 12/1997 |
| DE | 19751733 A1 | 12/1998 |
| DE | 19832634 A1 | 1/2000 |
| DE | 10019604 A1 | 10/2001 |
| DE | 10120942 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 544485 A1 | 6/1993 |
| EP | 0552576 A1 | 7/1993 |
| EP | 0611561 A1 | 8/1994 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 898944 A2 | 3/1999 |
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1 216 717 A1 | 6/2002 |
| EP | 1 216 718 A1 | 6/2002 |
| EP | 0693523 B1 | 11/2002 |
| EP | 1273312 A2 | 1/2003 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1674048 A1 | 6/2006 |
| EP | 1691606 A1 | 8/2006 |
| EP | 1782848 A2 | 5/2007 |
| EP | 2229918 A1 | 9/2010 |
| EP | 2 853 231 A1 | 4/2015 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2612392 A1 | 9/1988 |
| FR | 2715309 A1 | 7/1995 |
| FR | 2715405 A1 | 7/1995 |
| FR | 2 724 563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2859624 A1 | 3/2005 |
| FR | 2863277 A1 | 6/2005 |
| FR | 2876020 A1 | 4/2006 |
| FR | 2884706 A1 | 10/2006 |
| FR | 2929834 A1 | 10/2009 |
| FR | 2953709 A1 | 6/2011 |
| GB | 1174814 A | 12/1969 |
| GB | 2 051 153 A | 1/1981 |
| GB | 2306110 A | 4/1997 |
| JP | H0332677 A | 2/1991 |
| JP | H05237128 A | 9/1993 |
| JP | H09137380 A | 5/1997 |
| JP | H11146888 A | 6/1999 |
| JP | 2008538300 A | 10/2008 |
| JP | 2011078767 A | 4/2011 |
| WO | 89/02445 A1 | 3/1989 |
| WO | 89/08467 A1 | 9/1989 |
| WO | 90/12551 A1 | 11/1990 |
| WO | 92/06639 A2 | 4/1992 |
| WO | 92/20349 A1 | 11/1992 |
| WO | 93/11805 A1 | 6/1993 |
| WO | 9310731 A1 | 6/1993 |
| WO | 93/18174 A1 | 9/1993 |
| WO | 94/17747 A1 | 8/1994 |
| WO | 95/07666 A1 | 3/1995 |
| WO | 95/18638 A1 | 7/1995 |
| WO | 95/32687 A1 | 12/1995 |
| WO | 96/03091 A1 | 2/1996 |
| WO | 96/08277 A1 | 3/1996 |
| WO | 96/09795 A1 | 4/1996 |
| WO | 96/14805 A1 | 5/1996 |
| WO | 96/41588 A1 | 12/1996 |
| WO | 97/35533 A1 | 10/1997 |
| WO | 98/35632 A1 | 8/1998 |
| WO | 98/49967 A1 | 11/1998 |
| WO | 99/05990 A1 | 2/1999 |
| WO | 99/06079 A1 | 2/1999 |
| WO | 99/06080 A1 | 2/1999 |
| WO | 99/51163 A1 | 10/1999 |
| WO | 00/16821 A1 | 3/2000 |
| WO | 00/67663 A1 | 11/2000 |
| WO | 01/15625 A1 | 3/2001 |
| WO | 01/80773 A1 | 11/2001 |
| WO | 01/81667 A1 | 11/2001 |
| WO | 02/007648 A1 | 1/2002 |
| WO | 0217853 A2 | 3/2002 |
| WO | 00/078568 A1 | 10/2002 |
| WO | 03/002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 200511280 A1 | 2/2005 |
| WO | 2005013863 A2 | 2/2005 |
| WO | 2005018698 A1 | 3/2005 |
| WO | 2005048708 A1 | 6/2005 |
| WO | 2005105172 A1 | 11/2005 |
| WO | 2006018552 A1 | 2/2006 |
| WO | 2006023444 A2 | 3/2006 |
| WO | 2006032812 A2 | 3/2006 |
| WO | 2007048099 A2 | 4/2007 |
| WO | 2009031035 A2 | 3/2009 |
| WO | 2009071998 A2 | 6/2009 |
| WO | 2010043978 A2 | 4/2010 |
| WO | 2011007062 A1 | 1/2011 |
| WO | 2011026987 A1 | 3/2011 |
| WO | 2011038740 A1 | 4/2011 |

OTHER PUBLICATIONS

Langenbech, M. R. et al., "Comparison of biomaterials in the early postoperative period," Surg Endosc., May 2003, pp. 1105-1109, 17 (7).

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Klinge, U. et al., "Foreign Body Reaction to Meshes Used for the Repair of Abdominal Wall Hernias," Eur J. Surg, Sep. 1999, pp. 665-673, 165.

(56) References Cited

OTHER PUBLICATIONS

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).

Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.

Junge, K. et al., "Functional and Morphologic Properties of a Modified Mesh for Inguinal Hernia Repair," World J. Surg., Sep. 2002, pp. 1472-1480, 26.

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.

Welty, G. et al., "Functional impairment and complaints following incisional hernia repair with different polypropylene meshes," Hernia, Aug. 2001; pp. 142-147, 5.

Varum, K. et al., "In vitro degradation rates of partially N-acetylated chitosans in human serum," Carbohydrate Research, Mar. 1997, pp. 99-101, 299.

Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).

Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220,18(2).

Blondin, C. et al., "Inhibition of Complement Activation by Natural Sulfated Polysaccharides (Fucans) from Brown Seaweed," Molecular Immuol., Mar. 1994, pp. 247-253, 31(4).

Zvyagintseva, T. et al., "Inhibition of complement activation by water-soluble polysaccharides of some far-eastern brown seaweeds," Comparative Biochem and Physiol, Jul. 2000, pp. 209-215,126(3).

Rosen, M. et al., "Laparoscopic component separation in the single-stage treatment of infected abdominal wall prosthetic removal," Hernia, 2007, pp. 435-440, 11, published online Jul. 2007.

Amid, P., "Lichtenstein tension-free hernioplasty: Its inception, evolution, and principles," Hernia, 2004; pp. 1-7, 8, published online Sep. 2003.

Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).

Muzzarelli, R. et al., "Reconstruction of parodontal tissue with chitosan," Biomaterials, Nov. 1989, pp. 598-604, 10.

Haroun-Bouhedja, F. et al., "Relationship between sulfate groups and biological activities of fucans," Thrombosis Res., Dec. 2000, pp. 453-459, 100(5).

Blondin, C. et al., "Relationships between chemical characteristics and anticomplementary activity of fucans," Biomaterials, Mar. 1996, pp. 597-603, 17(6).

Strand, S. et al., "Screening of Chitosans and Conditions for Bacterial Flocculation," Biomacromolecules, Mar. 2001, 126-133, 2.

Kanabar, V. et al., "Some structural determinants of the antiproliferative effect of heparin-like molecules on human airway smooth muscle," Br. J. Pharmacol., Oct. 2005, pp. 370-777, 146(3).

Hirano, S. et al., "The blood biocompatibility of chitosan and N-acylchitosans," J. Biomed. Mater. Res., Apr. 1985, 413-417, 19.

Rao, B. et al., "Use of chitosan as a biomaterial: Studies on its safety and hemostatic potential," J. Biomed. Mater. Res., Jan. 1997, pp. 21-28, 34.

Prokop, A. et al., "Water Soluble Polymers for Immunoisolation I: Complex Coacevation and Cytotoxicity," Advances in Polymer Science, Jul. 1998, pp. 1-51, 136.

Collins, R. et al., "Use of collagen film as a dural substitute: Preliminary animal studies," Journal of Biomedical Materials Research, Feb. 1991, pp. 267-276, vol. 25.

Dr. S. Raz, "The Karl Mayer Guide to Tehnical Textiles," Jan. 2000, pp. 1-36, Obertshausen, Germany.

Chen, G. et al., "A Hybrid Network of Synthetic Polymer Mesh and Collagen Sponge," The Royal Society of Chemistry 2000, Chem. Commun., Jul. 2000, pp. 1505-1506.

European Search Report for EP 16305063.6 date of completion is Jul. 12, 2016 (4 pages).

* cited by examiner

PROSTHESIS FOR HERNIA REPAIR

CROSS-REFERENCE TO RELATED APPLICATIONS

This application claims benefit of and priority to European Patent Application Serial No. 16305063.6 filed Jan. 25, 2016, the disclosure of the above-identified application is hereby incorporated by reference in its entirety.

BACKGROUND OF THE INVENTION

The present invention relates to a prosthesis, for example a prosthesis for treating hernias of the abdominal wall, comprising a reinforcement layer capable of promoting tissue ingrowth, and two barrier layers capable of preventing post-surgical adhesions on the prosthesis and on the fixing means provided for fixing the prosthesis on the abdominal wall.

BRIEF SUMMARY OF THE INVENTION

The abdominal wall in humans is composed of fat and muscles interconnected by fascias. The abdominal wall forms the anterior enclosure of the abdominal cavity in which are lodged the viscera organs such as the intestines, the stomach, etc. . . . said viscera organs being enclosed in the peritoneum. It sometimes happens that a break in continuity occurs in the fascias, allowing part of the peritoneum to slip through and form a sac, or a hernia, containing either fat or part of the intestines, said sac protruding into the abdominal wall, thereby creating a defect in said wall and weakening it. Hernias or incisional hernias (a hernia occurring through a parietal surgical scar) show themselves in the form of a bulge at the surface of the skin and are classed, for example, as umbilical or ventral hernias or incisional hernias, depending on where they are located.

In order to repair a hernia defect, surgeons usually use a prosthesis comprising a reinforcement layer of tissue ingrowth material, said reinforcement layer replacing and/or strengthening the weakened anatomical tissues. The efficiency of the prosthesis, hence the ability to minimize the risks of recurrence, depends to a large extent on how well the prosthesis is fixed to the surrounding biological tissues.

The prosthesis may be fixated over, under or within the defect. When the prosthesis is fixed under the defect, it must be introduced in the abdominal cavity in the first place and then anchored to the abdominal wall.

One method of hernia repair involves open surgery, with incision of the skin and then of the abdominal wall. In such a surgery, the prosthesis is introduced in the implantation site via the incision made in the skin. However, in this type of surgery, the surgeon has little space to work in and poor visibility.

Document U.S. Pat. No. 7, 824, 420 describes prosthesis intended to be used for hernia repair in an open surgery procedure. The prosthesis described in this document comprises two layers of tissue ingrowth material, namely material permitting tissue adhesion, joined together at their periphery, one of the two layers being provided with a central opening. The prosthesis therefore forms a sort of pocket accessible via said central opening. The prosthesis is introduced in the implantation site via the incision of the skin and the hernia defect. The recessed layer is positioned facing the abdominal wall with its central opening facing the hernia defect, while the other layer is positioned facing the abdominal cavity. The fixing means and fixing tools are introduced into the pocket formed by the prosthesis via the incision of the skin, the hernia defect and the central opening of the prosthesis. The surgeon then fixes the prosthesis to the abdominal wall by attaching the tissue ingrowth material of the recessed layer to the abdominal wall. To do this, the surgeon fires fixing means through the tissue ingrowth material of the recessed layer and into the abdominal wall from the pocket formed by the prosthesis.

Another method of hernia repair involves laparoscopic surgery, wherein the prosthesis is conveyed in the abdominal cavity thanks to a trocar into which it is placed. The advantages of laparoscopic hernia repair include reduced pain and hospital stay, rapid convalescence, quicker return to work, better functional and cosmetic results. In laparoscopic surgery, the abdominal cavity is insufflated in order to create adequate space therein for the surgeon to handle, position and anchor the prosthesis to the abdominal wall with the help of tools introduced in the abdominal cavity via additional trocars. Such a surgery is known as the intraperitoneal route as the prosthesis is positioned on the abdominal wall from the "inside" of the peritoneum, namely from the inside of the abdominal cavity.

In such procedures, one face of the prosthesis bears on the abdominal wall while the opposite face of the prosthesis faces the viscera organs which are present in the abdominal cavity. It may then happen that following the surgical operation, some of the viscera organs adhere via a fibrin bridging mechanism to some parts of the prosthesis that face the abdominal cavity, such as for example the tissue ingrowth material forming the prosthesis and/or some of the fixing means used for fixing the prosthesis to the abdominal wall. Such a phenomenon may lead to risks for the patient such as transit dysfunction, occlusion or necrosis. In order to avoid these potential post-operative adhesions, a barrier layer is usually provided on the face of the prosthesis that is intended to face the abdominal cavity.

Anyway, it has been observed that the intraperitoneal repair of hernia defect could still lead to postoperative complications and early recurrences, in particular because of the exposure of the viscera organs to the parts of the prosthesis that face the abdominal cavity.

There is therefore the need for a prosthesis for the treatment of hernia, that would limit the potential postoperative complications due to the proximity between the prosthesis fixed to the abdominal wall and the viscera organs present in the abdominal cavity.

The present invention aims at providing a prosthesis for the treatment of hernia, in particular via the laparoscopic route, said prosthesis having a specific structure allowing it to minimize the risks of attachment of the viscera organs to the prosthesis posterior to the implantation of the prosthesis and to its fixation to the abdominal wall.

A first aspect of the invention is a prosthesis for treating a hernia defect in the abdominal wall comprising :

At least one reinforcement layer, comprising a biocompatible porous material, said reinforcement layer including a first surface intended to face the abdominal wall and a second surface opposite said first surface, said reinforcement layer being delimited by an outer edge, At least one first barrier layer, comprising a biocompatible anti-adhesion material, said first barrier layer including a first surface and a second surface opposite said first surface of the first barrier layer, the first surface of the first barrier layer covering substantially at least a central part of the area of the second surface of said reinforcement layer, the second surface of said first barrier layer being intended to face the abdominal cavity, said first barrier layer being delimited by a peripheral outer edge, At least one second barrier layer, said second barrier layer being shaped and dimensioned so as to cover at least the part of the area of the second surface of said reinforcement layer that is not covered by the first barrier layer, said second barrier layer being formed of one or more flap members, each flap member being formed of a piece of sheet of biocompatible anti-adhesion material and having at least an outer edge attached to the second surface of the reinforcement layer, and a free inner edge.

Within the meaning of the present application, "porous material" is understood as a material having pores, voids or holes, that are open and are distributed uniformly or irregularly and promote cell colonization and tissue ingrowth. The pores can be present in all types of configurations, for example as spheres, channels, hexagonal forms.

Within the meaning of the present application, "anti-adhesion material" is to be understood as meaning a biocompatible material that exhibits a continuous and smooth surface, for example non-porous, that minimizes tissue attachment by preventing providing space for cell recolonization, at least for the time period corresponding to the time during which post-surgical adhesions are likely to occur.

In the present application, the terms "outer" and "inner" are to be understood with respect to the prosthesis itself. For example, whatever the shape of the prosthesis, "inner" means in the direction of the centre of the prosthesis while "outer" refers to the direction towards the periphery and exterior of the prosthesis.

The prosthesis of the invention allows forming one or more protected spaces for positioning the fixing means intended to attach the prosthesis to the abdominal wall in a way allowing that said fixing means are prevented from entering in contact with the viscera organs present in the abdominal cavity at least for the time period corresponding to the time during which post-surgical adhesions are likely to occur. In particular, the structure of the second barrier layer of the prosthesis of the invention, which is formed of one or more flap members, allows creating protected spaces, adequate for positioning fixing means, such as clips, tacks, screws, spirals, straps, staples, suture or transfacial sutures, in a way that said fixing means are separate from the abdominal cavity, and in particular from the viscera organs present in said abdominal cavity, by a protective layer preventing adhesions at least for the time period corresponding to the time during which post-surgical adhesions are likely to occur after the implantation of the prosthesis, said protective layer being formed of the one or more flap members. Moreover, the fact that the second barrier layer is formed of one or more flap members provides for an easy access to said protected spaces for the surgeon. Thanks to the shape and nature of the second barrier layer of the prosthesis of the invention, the surgeon may easily fire fixing means, such as tacks, underneath the flap member(s), at the right position for fixing safely the prosthesis to the abdominal wall, and with limited risks that said fixing means further generate post-surgical adhesions with the organs of the abdominal cavity.

The prosthesis of the invention therefore allows completing intraperitoneal hernia repair with fewer risks of recurrence or of postoperative complications.

The prosthesis of the invention allows protecting the intestine and hollow organs of the abdominal cavity while efficiently strengthening the abdominal wall.

The prosthesis of the invention comprises at least one reinforcement layer, comprising a biocompatible porous material, said reinforcement layer including a first surface intended to face the abdominal wall and a second surface opposite said first surface. In embodiments, the reinforcement layer may consist in said biocompatible porous material.

The porous material suitable for the reinforcement layer of the prosthesis of the invention may comprise a sponge, a fibrous matrix or a combination of a sponge and of a fibrous matrix. For example, the sponge can be obtained by lyophilization of a gel, with pores being created during the lyophilization. The fibrous matrix can be any arrangement of yarns or yarn portions creating pores between the yarns and/or yarn portions. For example, the fibrous matrix can be a textile, for example obtained by knitting or weaving or according to a technique for producing a nonwoven.

In embodiments, the porous material, for example the sponge and/or the fibrous matrix, has pores with dimensions ranging from approximately 0.1 to approximately 3 mm.

In embodiment, the porous material comprises, preferably consists in, a mesh.

Within the meaning of the present application, a "mesh" is understood as an arrangement of biocompatible yarns, such as a knit, a woven fabric, a non-woven fabric, open-worked, that is to say provided with pores that favour recolonization of tissue. Such a mesh can be bioresorbable, permanent or partially bioresorbable. It is sufficiently flexible to be folded up and inserted into a trocar at the time of introduction into the abdominal cavity. The mesh can be made from one layer of textile or several layers of textiles. Such meshes are well known to a person skilled in the art. The mesh that can be used according to the invention can be supplied in any shape whatsoever, for example rectangular, square, circular, oval, etc., and can then be cut to suit the shape of the hernia defect. For example, the mesh can have a generally square shape or a rectangular shape. Alternatively, the overall shape of the mesh can be circular or oval.

In one embodiment of the invention, the mesh is a knit. By virtue of the meshwork of the knit, it is possible to obtain openworked faces that promote cell recolonization after implantation. The knit can be two-dimensional or three-dimensional.

Within the meaning of the present application, a two-dimensional knit is understood as a knit having two opposite faces linked to each other by meshes but devoid of a spacer giving it a certain thickness: such a knit can be obtained, for example, by knitting yarns on a warp knitting machine or raschel knitting machine using two guide bars. Examples of knitting two-dimensional knits suitable for the present invention are given in the document WO2009/071998.

According to the present application, a three-dimensional knit is understood as a knit having two opposite faces linked to each other by a spacer that gives the knit a significant thickness, said spacer itself being formed from additional linking yarns in addition to the yarns forming the two faces of the knit. Such a knit can be obtained, for example, on a double-bed warp knitting or raschel knitting machine using several guide bars. Examples of knitting three-dimensional knits suitable for the present invention are given in the documents WO99/05990, WO2009/031035 and WO2009/071998.

The porous material may comprise a bioresorbable or non-bioresorbable material.

In the present application, "bioresorbable" or "biodegradable" is understood to mean that the materials having this property are absorbed and/or degraded by the tissues or washed from the implantation site and disappear in vivo after a certain time, which may vary, for example, from a few hours to a few years, depending on the chemical nature of the materials.

The bioresorbable material suitable for the porous material of the reinforcement layer can be chosen from among the following bioresorbable materials: polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), polyethylene glycol (PE), copolymers of these materials, and mixtures thereof.

The non-bioresorbable material suitable for the porous material of the reinforcement layer can be chosen from among the following non-bioresorbable materials: polypropylenes, polyesters such as polyethylene terephthalates, polyamides, silicones, polyether ether ketone (PEEK), polyarylether ether ketone (PAEK) and mixtures thereof.

In one embodiment of the invention, the reinforcement layer of porous material can be made from a gripping textile. Examples of gripping textile are described in the document WO/0181667. For example, with said gripping textile having a face provided with barbs, said face provided with barbs can be directed towards the biological tissues, for example the abdominal wall, for helping in the fixing of the prosthesis to the abdominal wall.

The reinforcement layer may exhibit any shape as long as said shape is large enough so as to cover efficiently the hernia defect to be treated.

In embodiments, said reinforcement layer has the shape of a rectangle, with or without rounded corners. In other embodiments, the reinforcement layer may have an oval shape. Such embodiments are suitable, for example, for the treatment of a ventral hernia. In embodiments, the reinforcement layer has the shape of a disc. Such an embodiment is suitable, for example, for the treatment of an umbilical hernia.

By virtue of its porous character, the reinforcement layer of the prosthesis of the invention is especially adapted to promote tissue ingrowth via its first surface after implantation. The cells of the abdominal wall deeply colonize the porous structure of the reinforcement layer via the first surface of the prosthesis.

The prosthesis of the invention further comprises at least a first barrier layer comprising a biocompatible anti-adhesion material, the first barrier layer including a first surface and a second surface opposite said first surface of the first barrier layer, the first surface of the first barrier layer covering substantially at least a central part of the area of the second surface of the reinforcement layer, the second surface of said first barrier layer being intended to face the abdominal cavity, said first barrier layer being delimited by a peripheral outer edge. In embodiments, the first barrier layer consists in said biocompatible anti-adhesion material.

The first barrier layer is positioned in the prosthesis of the invention so as to face the abdominal cavity and prevent the organs and other viscera of the abdominal cavity from attaching themselves at least to a central part of the prosthesis. The first barrier layer may adopt any shape, oval, circular, rectangular, etc. so as to substantially cover the central region of the second surface of the reinforcement layer. As will appear from the description below, the second barrier layer will cover the remaining part of the area of the second surface of the reinforcement layer, in other words the part of the area of the second surface of the reinforcement layer that is not covered by the first barrier layer, so that the entire area of the second surface of the reinforcement layer of the prosthesis is in the end covered by anti-adhesion material, either from the first barrier layer or from the second barrier layer.

In embodiments, the first barrier layer may cover the entire area of the second surface of the reinforcement layer. In embodiments, the first barrier layer may extend beyond the outer edge of the reinforcement layer, for example on a distance ranging from 3 mm to 7 mm. The viscera organs present in the abdominal cavity are therefore well prevented from contacting any porous material forming the reinforcement layer.

As seen above, the anti-adhesion material suitable for the first barrier layer is a biocompatible material that exhibits a continuous and smooth surface, for example non-porous, that minimizes tissue attachment by preventing providing space for cell recolonization, at least for the time period corresponding to the time during which post-surgical adhesions are likely to occur.

Such an anti-adhesion material makes it possible in particular to avoid the formation of undesirable and serious post-surgical fibrous adhesions, for example when the prosthesis is implanted in an intraperitoneal location.

The anti-adhesion material may be chosen from among bioresorbable materials, non-bioresorbable materials and mixtures thereof. The non-bioresorbable anti-adhesion materials can be selected from among polytetrafluoroethylene, polyethylene glycols, polysiloxanes, polyurethanes, and mixtures thereof.

Said anti-adhesion material is preferably bioresorbable: the bioresorbable materials suitable for said anti-adhesion material can be selected from among collagens, oxidized celluloses, polyethylene glycol, polyacrylates, trimethylene carbonates, caprolactones, dioxanones, butyric or glycolic acid, lactic acid, glycolides, lactides, polysaccharides, for example chitosans, polyglucuronic acids, hyaluronic acids, dextrans, polyvinyl alcohol, polypeptides, polymers, copolymers and mixtures thereof.

The anti-adhesion material suitable for the first barrier layer makes it possible to protect at least the central part, in embodiments the entire, area of the reinforcement layer of the prosthesis, at least during the initial phase of healing, that is to say the reinforcement layer is not exposed to inflammatory cells such as granulocytes, monocytes, macrophages or even the multi-nuclear giant cells that are generally activated by the surgery.

In the case where the anti-adhesion material is made of non-bioresorbable materials, it thus protects the reinforcement layer before and after implantation, throughout the period of implantation of the prosthesis.

Moreover, by virtue of the anti-adhesion material, the fragile surrounding tissues such as the hollow viscera, for example, are protected particularly from the formation of serious and undesirable post-surgical fibrous adhesions.

In the case where the anti-adhesion material comprises a bioresorbable material, it is preferable to choose a bioresorbable material that is resorbed only after a period of time ranging from a few days to a few weeks, so as to ensure that the anti-adhesion material can perform its function of protecting the intestine and the hollow organs during the days after the operation and until the cell recolonization of the prosthesis in turn protects the fragile organs.

The anti-adhesion material forming the first barrier layer may for example be provided as a coating or a film.

In embodiments, the first barrier layer is a coating. For example, a solution or suspension of an anti-adhesion material, for example polycaproplactone, is prepared by solubilising said anti-adhesion material in a solvent. The solution or suspension may then be applied on the part of the area of the second surface of the reinforcement layer that is intended to be covered by the first barrier layer, for example at least a central part of the area of said second surface or alternatively the entire area of said second surface. For example, the solution or suspension may be sprayed over the area to be coated in order to form a homogeneous coating. The spraying step may be repeated until the desired amount of material is deposed on the second surface of the reinforcement layer. The solvent may be evaporated during the coating process.

In other embodiments, the first barrier layer may be under the form of a film of anti-adhesion material that is further applied on the area of the second surface of the reinforcement layer to be covered.

For example, a film suitable for the first barrier layer of the prosthesis of the invention is described in U.S. Pat. No. 6,235,869 and may be prepared as follows : a copolymer of glycolide, lactide, trimethylene carbonate and e-caprolactone is synthetized and provided under the form of pellets. The pellets are melt and extruded as a film with a controlled thickness. For example, the film thickness is between 0.5 to 1.2 mil.

The film may be applied on the second surface of the reinforcement layer as follows : the reinforcement layer is placed in a lamination equipment with its second surface at the top. The film prepared as above described is positioned upon the second surface of the reinforcement layer on the part of the area of the second surface of the reinforcement layer that is intended to be covered by the first barrier layer, for example at least a central part of the area of said second surface or alternatively the entire area of said second surface. The assembly may then be pressed under controlled conditions of temperature and pressure so as to laminate the film on the second surface of the reinforcement layer.

The prosthesis of the invention further comprises at least a second barrier layer, said second barrier layer being shaped and dimensioned so as to cover at least the part of the area of the second surface of said reinforcement layer that is not covered by the first barrier layer, said second barrier layer comprising one or more flap members, each flap member being formed of a piece of sheet of biocompatible anti-adhesion material, and having at least an outer edge attached to the second surface of the reinforcement layer and a free inner edge.

In the present application, by "flap member" is meant a piece of sheet of biocompatible anti-adhesion material having any shape, such as rectangular, annular, triangular, square, said shape defining an outer edge and an inner edge of said flap member, said outer edge being attached to the second surface of the reinforcement layer, said inner edge being left free, so that the flap member is able to adopt a rest configuration, in which the piece of sheet is substantially parallel to the reinforcement layer, with the inner edge of the flap member being in the direction of the centre of the reinforcement layer, and a lifted configuration, in which the inner edge of the flap member is pulled away from the reinforcement layer.

In embodiments, the second barrier layer consists in said one or more flap members.

The areas of the pieces of sheet of biocompatible anti-adhesion material of the flap member(s) forming the second barrier layer amount altogether, in a rest configuration of the flap members, namely parallel to the reinforcement layer, to a total area corresponding to at least the area of the second surface of the reinforcement layer that is not covered by the first barrier layer, also hereinafter referred to as the "remaining area". Some of the flap members may overlap with others. In any case, the second barrier layer being shaped and dimensioned so as to cover at least the part of the area of the second surface of the reinforcement layer that is not covered by the first barrier layer, in the end, the whole surface of the "remaining area" is safely covered by anti-adhesion material. As a result, the entire area of the second surface of the reinforcement layer is covered by anti-adhesion material, coming either from the first barrier layer or from the second barrier layer.

In embodiments, the area resulting from the addition of the areas of the one or more flap member(s) is less than 120% of the area of the second surface of said reinforcement layer that is not covered by the first barrier layer, namely the remaining area. Implantation of excess foreign material within the body of the patient is therefore avoided, while ensuring that the entire area of the second surface of the reinforcement layer is safely covered by anti-adhesion material.

The flap member(s) of the second barrier layer is/are further intended to cover the proximal ends of the fixing means, for example the heads of the tacks, that will be fired through the reinforcement layer in a view of fixating the prosthesis to the abdominal wall. The piece of sheet of anti-adhesion material forming one flap member is therefore preferably shaped and dimensioned so as to cover entirely at least the proximal end of one fixing means, for example the head of a tack, that will protrude from the prosthesis once the prosthesis is fixed to the abdominal wall. In embodiments, one flap member may be formed of a piece of sheet shaped and dimensioned so as to cover a plurality of fixing means, in particular the proximal ends of said fixing means, such as tacks' heads, protruding out of the second surface of the reinforcement layer once the prosthesis is fixed to the abdominal wall.

In this application, the distal end of a device must be understood as meaning the end furthest from the hand of the user and the proximal end must be understood as meaning the end closest to the hand of the user.

For example, whatever the shape of the piece of sheet forming a flap member, it is recommended that the smallest dimension of said shape correspond at least to twice the length of the fixing means used to fixate the prosthesis to the abdominal wall, for example twice the length of the tack used.

In embodiments, the smallest dimension of the shape of the piece of sheet of anti-adhesion material forming a flap member ranges from about 1 cm to 4 cm, preferably from 2 cm to 3 cm.

In embodiments, the second barrier layer comprises at least a first flap member having the form of an annular band, the outer edge of said first flap member being substantially attached to the second surface of the reinforcement layer along the outer edge of said reinforcement layer.

The position of the attaching line of the outer edge of the first flap member may vary between the outer edge of the reinforcement barrier layer and a line offset slightly from said outer edge, towards the center of the prosthesis, this attaching line being substantially parallel to the outer edge of the reinforcement layer.

The inner edge of the first flap member being free, the first flap member forms a sort of skirt attached along the outer edge of the reinforcement layer, said skirt allowing access to an annular protected space defined between the skirt and the reinforcement layer. At the time of fixating the prosthesis to the abdominal wall, the surgeon will be able to gain access easily to the protected space by lifting the free inner edge of the skirt shaped flap member, to introduce the fixating tool therein and fire therein the tacks. As a result, the heads of the tacks will be covered by the skirt formed by the first flap member, namely by the anti-adhesion material piece of sheet forming the first flap member, so that the heads of the implanted tacks will not be in contact with the surrounding biological organs, at least during the time period corresponding to the time during which post-surgical adhesions are likely to occur. Because of the annular band shape of the skirt shaped flap member, the surgeon will be able to fire tacks all along the perimeter of the reinforcement layer and will be able to distribute the tacks as desired along this perimeter for an optimal fixation.

Because of the fact that the first flap member forming the second barrier layer is attached to the reinforcement layer along the outer edge of the reinforcement layer, for example at a distance of about 1 cm from the outer edge of the reinforcement layer, the surgeon can safely push the fixating tool to the very end of the protected space, at the location where the second barrier layer and the reinforcement layer are attached together, and fire the tack so as to fix the reinforcement layer to the abdominal wall. The surgeon may repeat this step as many times as needed all along the periphery of the line attaching the second barrier layer to the reinforcement layer. Suitable fixing means include resorbable or non-resorbable clips, tacks, screws, spirals, straps, staples, suture or transfacial sutures. Thus, the surgeon is assured of fixing the prosthesis to the biological tissues, for example the abdominal wall or peritoneum, without any risk of touching and/or stapling the surrounding organs, for example the intestines.

Moreover, once the surgeon has fixed the reinforcement layer of the prosthesis to the abdominal wall and the fixing tool has been removed from the implantation site, the heads of the tacks which have been positioned for fixing the prosthesis to the abdominal wall are located in the protected space delimited inbetween the second barrier layer and the reinforcement layer. As a consequence, the heads of the tacks are covered by the second barrier layer, in particular by the flap member(s) forming the second barrier layer, and are not in contact with the viscera organs present in the abdominal cavity.

In embodiments, said second barrier layer consists in said first flap member having the form of an annular band, the outer edge of said first flap member being substantially attached to the second surface of the reinforcement layer along the outer edge of said reinforcement layer. As described above, in such a case, the first flap member covers at least the part of the area of the second surface of said reinforcement layer that is not covered by the first barrier layer, namely the remaining area. In embodiments, the first flap member may have an area greater than the remaining area and it may therefore overlap a part of the first barrier layer. In any case, the entire area of the second surface of the reinforcement layer is covered by anti-adhesion material.

In other embodiments, the second barrier layer further comprises at least a second flap member in addition to said first flap member, the outer edge of said second flap member being substantially attached to the second surface of the reinforcement layer along a line located between the outer edge of the reinforcement layer and the outer edge of the first barrier layer. The presence of additional flap members allows creating additional protected spaces for firing fixing means, for a reinforced fixation. The additional flap members may be positioned in function of the location of the reinforcement layer where a reinforced fixation may be needed. Reinforced fixations may be needed for example in case of large prosthesis intended to be implanted in obese patients.

For example, the second barrier layer may consist in a first flap member having the form of a first annular band, the outer edge of said first flap member being substantially attached to the second surface of the reinforcement layer along the outer edge of said reinforcement layer, and in a second flap member, said second flap member having the form of a second annular band, said first and second flap members being concentrically positioned one with respect to the other, so that the outer edge of said second flap member is substantially attached to the second surface of the reinforcement layer along a line substantially parallel to the outer edge of the reinforcement layer, said line being located between the outer edge of the reinforcement layer and the outer edge of the first barrier layer.

As described above, in such a case, the first flap member and the second flap member cover at least the part of the area of the second surface of said reinforcement layer that is not covered by the first barrier layer, namely the remaining area. In embodiments, the first flap member and the second flap member may together totalize an area greater than the remaining area. For example, the free inner edge of the first flap member may overlap the attached outer edge of the second flap member, and the free inner edge of the second flap member may overlap the outer edge of the first barrier layer. In any case, the entire area of the second surface of the reinforcement layer is covered by anti-adhesion material.

In such embodiments, the second flap member defines a second skirt, in addition to the first skirt defined by the first flap member, allowing access to a second annular protected space defined between the second skirt and the reinforcement layer, concentrically located with the first annular protected space created by the first flap member in the direction of the center of the reinforcement layer.

Such embodiments allow the surgeon to position a first line of tacks at the location of the first protected space and a second line of tacks at the location of the second protected space, for example for a reinforced fixation of the prosthesis.

Alternatively, for example, the second barrier layer may consist in a first flap member having the form of an annular band, the outer edge of said first flap member being substantially attached to the second surface of the reinforcement layer along the outer edge of said reinforcement layer, and in a second and a third flap members, each of said second and third flap members having the form of a tape portion, the respective outer edges of said second and third flap members being substantially attached to the second surface of the reinforcement layer along line(s) located between the outer edge of the reinforcement layer and the outer edge of the first barrier layer, said line(s) being intended to be positioned in regards of the vicinity of the edges of the hernia defect.

Such embodiments allow proceeding to a fixation technique where additional tacks may be positioned at the vicinity of the edges of the defect to be treated.

In embodiments, the outer edge of said first flap member is attached along the outer edge of said reinforcement layer in a continuous way. The surgeon therefore knows that he can apply the tacks or the staples at any point in the space created inbetween the first flap member and the reinforcement layer, without having to look for a precise location.

In embodiments, the outer edge of said first flap member is attached to the second surface of the reinforcement layer so as to define an attaching line which is offset towards a center of the prosthesis from about 0.5 to about 2 cm, preferably about 1 cm, from the outer edge of said reinforcement layer. Such embodiments allow ensuring that the fixing means, such as the clips, tacks, screws, spirals, straps, staples, suture or transfacial sutures, will not move closer to the outer edge of the prosthesis and in particular of the reinforcement layer, than 1 cm. The surgeon is therefore ensured that the fixing means will be positioned so as to guaranty an efficient fixing. It may then be useful that the first barrier layer covers the entire area of the second surface of the reinforcement layer, and optionally goes beyond the outer edge of the reinforcement layer, to ensure that the entire area of the second surface of the reinforcement layer is covered by anti-adhesion material.

In embodiments, said first barrier layer covering the entire area of the second surface of the reinforcement layer, the outer edge(s) of the flap member(s) forming the second barrier layer is/are attached to the second surface of the reinforcement layer via the intermediate of the first barrier layer.

In embodiments, the outer edge(s) of the flap member(s) forming the second barrier layer is/are attached to the second surface of the reinforcement layer by attaching means selected from the group comprising ultrasonic welding, hot compression welding, gluing and combinations thereof.

For example, when the first barrier layer is intended to cover the entire area of the second surface of the reinforcement layer and when the second barrier layer is intended to consist in one flap member having the form of an annular band, the first and second barrier layers may be attached one to the other in a separate step, the assembly of the two attached layers being thereafter attached to the reinforcement layer.

The step of attaching the first barrier layer to the second barrier layer may be performed by ultrasonic welding as follows: a layer of the first barrier layer is placed on an ultrasonic press anvil, the anvil being protected by a peelable film of a polymer having a melting point higher than the temperature intented to be set for the lamination step, said peelable film being intended to prevent the welding of the first barrier layer on the ultrasonic press anvil. A second peelable film of the same polymer, shaped into a similar but smaller shape than the future first barrier layer, is laid on the first barrier layer so as to let non protected only a peripheral region of the first barrier layer.

The annular band shaped second barrier layer is placed onto the second peelable film, so as to overlap both the unprotected peripheral region of the first barrier layer and a peripheral region of the second peelable film. A third peelable film of the same polymer as above, having the same shape of the second barrier layer is laid on the top of the second barrier layer to prevent the welding of the second barrier layer on the ultrasonic press sonotrod.

The sonotrod of the ultrasonic welding press is lowered to press the second barrier layer onto the first barrier layer. Ultrasonic vibration is applied, and the second barrier layer is welded to the future first barrier layer in the peripheral region of the first barrier layer.

The first peelable film is removed, and the assembly of the first and second barrier layers is afterward placed on the second surface of the reinforcement layer coated with a polymer glue.

A hot press is then used to apply a pressure onto the three layers so as to hotmelt the gluing polymer coating and glue the first barrier layer onto the reinforcement layer. Because of the presence of the second and third peelable antiadhesion films, the second barrier layer is prevented to adhere onto the first barrier layer and onto the hot press.

By removing the second and third peelable films, a prosthesis of the invention is obtained, in which the first barrier layer covers the entire area of the second surface of the reinforcement layer and the second barrier is an annular band shaped flap member, the outer edge of which is attached to the first barrier layer and therefore to the reinforcement layer. In other words, the outer edge of the second barrier layer is attached to the reinforcement layer via the intermediate of the first barrier layer.

In the prosthesis of the invention, the second barrier layer is strongly assembled with the first barrier layer and/or the reinforcement layer and the integrity of the assembly is not compromised by the movement of the tacker shaft in the protected space created by the second barrier layer at the moment the surgeon proceeds to the fixing of the prosthesis to the abdominal wall.

The anti-adhesion material suitable for forming the second barrier layer may be defined in the same way as the anti-adhesion material defined above for the first barrier layer. The anti-adhesion material used for forming the second barrier layer may be identical or different from that used for forming the first barrier layer. Moreover, the anti-adhesion material used for forming the flap member(s) of the second barrier layer may be identical or different from one flap member to the other.

The anti-adhesion material forming the flap members(s) of the second barrier layer makes it possible to protect at least the remaining area, in other words, the part of the area of the second surface of said reinforcement layer that is not covered by the first barrier layer, at least during the initial phase of healing, that is to say the reinforcement layer is not exposed to inflammatory cells such as granulocytes, monocytes, macrophages or even the multi-nuclear giant cells that are generally activated by the surgery.

Indeed, at least during the initial phase of healing, the duration of which can vary between 5 and 10 days approximately, only the anti-adhesion material of the first barrier layer and of the second barrier layer can be accessed by the various factors such as proteins, enzymes, cytokines or cells of the inflammatory line.

For example, the flap member(s) forming the second barrier layers may be pieces of films of anti-adhesion material as described above for the first barrier layer.

In embodiments, said second barrier layer is provided with markings intended to indicate to the surgeon where to locate one or more fixing means for fixing the prosthesis to the abdominal wall. For example, said markings may be under the form of colored spots located on the surface of said second barrier layer intended to face the abdominal cavity. In embodiments, the markings, such as colored spots, are regularly spaced from one another along a perimeter of said second barrier layer. For example, the markings are distant 1.5 cm from one another. Such embodiments allow the surgeon to easily position the fixing means, such as tacks, at intervals of 1.5 cm. Such a fixation technique is usually associated with a low recurrence rate of the hernia (see Bittner, R., et al., *Guidelines for laparoscopic treatment of ventral and incisional abdominal wall hernias (International Endohernia Society (IEHS)—Part* 1. Surgical Endoscopy, 2014. 28(1): p. 2-29)

In embodiments, the second barrier layer may be provided with identification means for distinguishing said second barrier layer from said first barrier layer. For example, the second barrier layer may show a color different than that of the first barrier layer. In other examples, the second barrier layer may be provided with specific designs drawn on flap member(s), such as geometric figures, etc . . .

In embodiments, the free inner edge(s) of said flap member(s) forming the second barrier layer is/are provided with one or more projecting tab(s) intended to help the surgeon lift said flap member(s) from said reinforcement layer. Such embodiments allow the surgeon lift easily the flap member in order to introduce the fixing means within the protected space formed between the flap member and the reinforcement layer. The gesture of the surgeon is therefore facilitated.

In embodiments, the flap member(s) forming the second barrier layer is/are provided on their surface regarding the reinforcement layer or the first barrier layer with a tacky layer of biocompatible materials capable of sticking to said reinforcement layer or first barrier layer. It is therefore possible to stick the flap member(s) to the reinforcement layer or first barrier layer once the fixing means has been positioned, the flap member(s) thereby covering the proximal ends of the fixing means with reinforced safety. The biocompatible materials suitable for forming the tacky layer may be selected from collagen-based, polylactone-based, polylactic, polyethylene glycol, polysaccharides and/or polyvinyl alcohol based surgical adhesives, fibrin glues, and combinations thereof.

Another aspect of the invention is a method for treating a hernia defect, in particular a ventral hernia defect, comprising the following steps:
 a prosthesis as disclosed herein is provided,
 the prosthesis is conveyed into the abdominal cavity after the hernia sac has been reduced, for example by means of a trocar,
 the prosthesis is fixed to the abdominal wall with the first surface of the reinforcement layer facing the abdominal wall, by means of tacks fired in the protected space created between the first barrier layer and the second barrier layer, so that, once the prosthesis is fixed, the second barrier layer covers the heads of the tacks, thereby preventing the viscera organs from entering in contact with the tacks.

BRIEF DESCRIPTION OF THE DRAWING

The present invention will become clearer from the following description and from the attached drawings, in which.

DETAILED DESCRIPTION OF THE INVENTION

Figure 1:
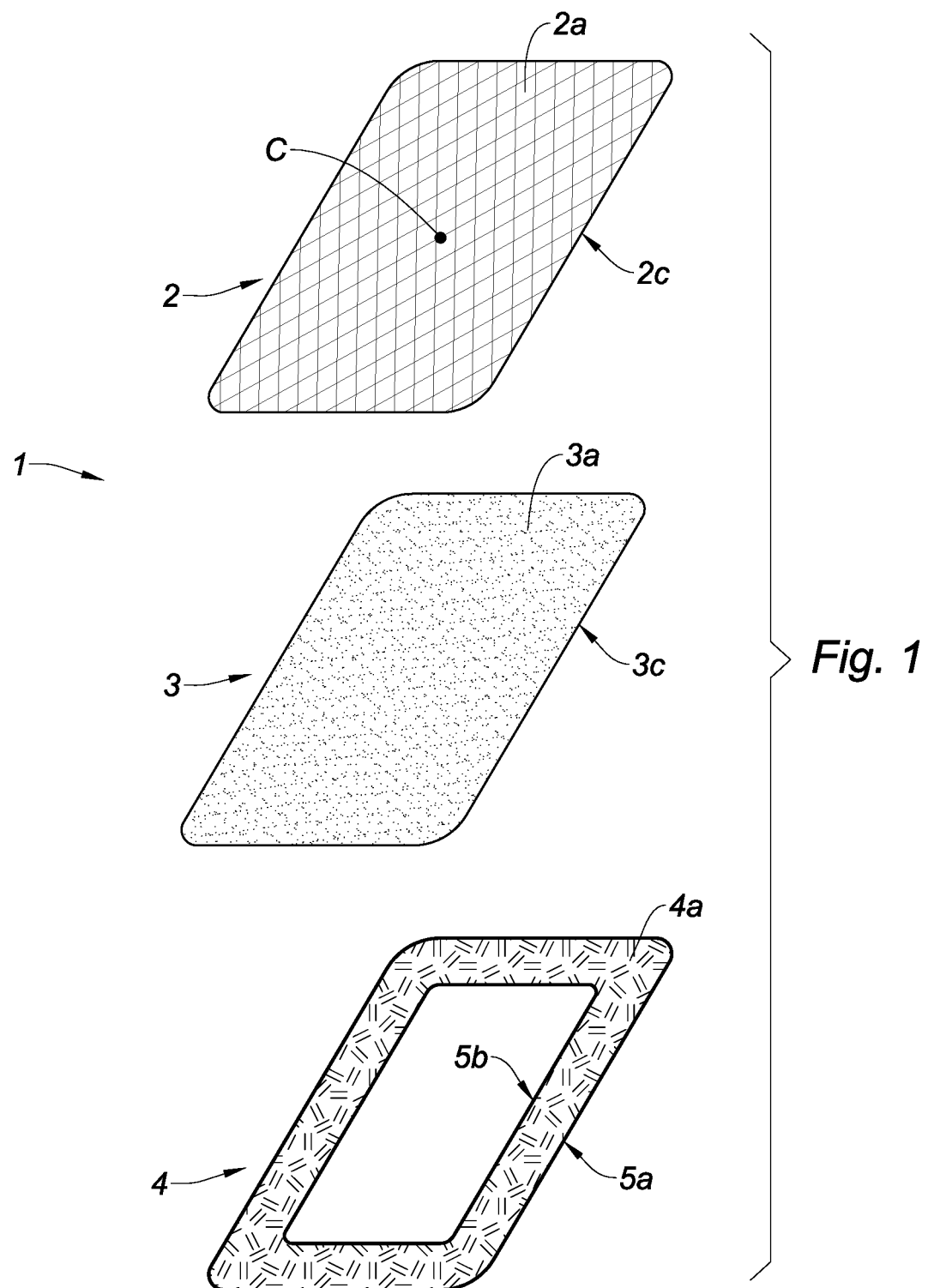
FIG. 1 is an exploded view of a first embodiment of the prosthesis of the invention.
Figure 2:
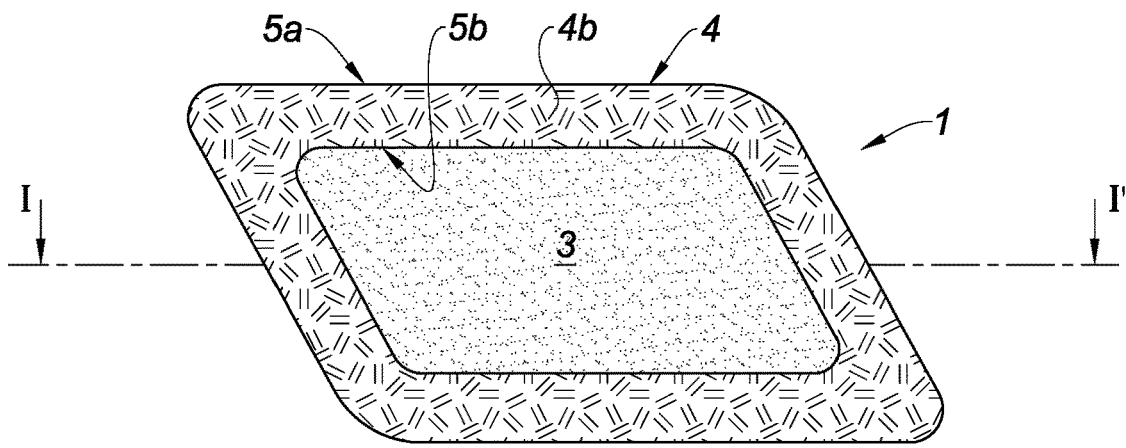
FIG. 2 is a bottom perspective view of the prosthesis of FIG. 1.
Figure 3:
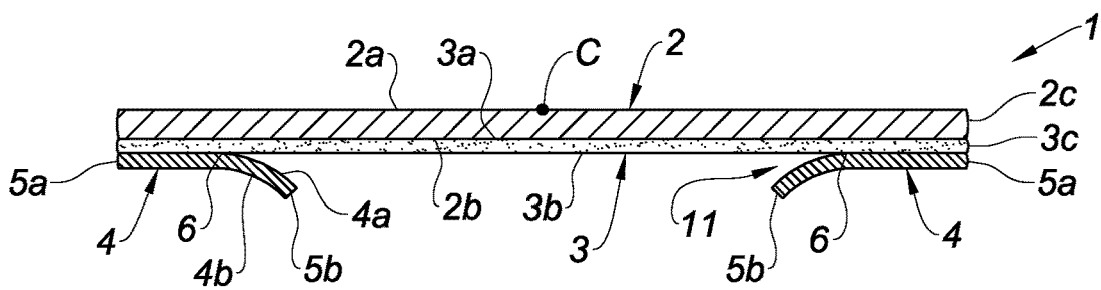
FIG. 3 is a cross sectional view of the prosthesis of FIG. 2 taken along plane I-I'.

With reference to FIGS. 1-3 is shown a prosthesis 1 in accordance with the present invention intended to be used in the treatment of hernia, in particular ventral hernia, via the laparoscopic route. The prosthesis 1 comprises a reinforcement layer 2, intended to provide strength and mechanical properties to the prosthesis 1, a first barrier layer 3 intended to limit and prevent the formation of adhesions between the reinforcement layer 2 and the organs of the abdominal cavity (see FIGS. 10-12), and a second barrier layer 4 intended to prevent the formation of adhesions between the organs of the abdominal cavity 109 and the fixing means for fixing the prosthesis 1 to the abdominal wall 104.

The reinforcement layer 2 is made of a biocompatible porous material, in particular capable of promoting tissue ingrowth. The reinforcement layer may be under the form of a sponge, for example obtained by lyophilisation of a polymeric composition, a fibrous matrix such as a textile or combinations thereof. The reinforcement layer preferably shows mechanical properties allowing it to perform its function of strengthening and repairing the abdominal wall.

Reinforcement layers are well known in the art. In embodiments, the reinforcement layer may be a textile, such as a bidimensional porous knit or a three-dimensional porous knit.

With reference to FIGS. 1-3, the reinforcement layer 2 has the shape of a rectangle, with rounded corners. In other embodiments, the reinforcement layer may have an oval shape. Such embodiments are suitable, for example, for the treatment of a ventral hernia. In embodiments, the reinforcement layer has the shape of a disc. Such an embodiment is suitable, for example, for the treatment of an umbilical hernia. The reinforcement layer may exhibit any shape as long as said shape is large enough so as to cover efficiently the hernia defect to be treated.

The reinforcement layer 2 has a first surface 2a and a second surface 2b, opposite the first surface. On the example shown, the first surface 2a is intended to face the abdominal wall (see FIGS. 10-12). The reinforcement layer 2 is delimited by an outer edge 2c and has a center C.

The prosthesis 1 further comprises a first barrier layer, under the form of a film 3 on the example shown. The first barrier layer or film 3 is made of a biocompatible anti-adhesion material. The film 3 shows a first surface 3a and a second surface 3b, opposite the first surface 3a. The first barrier layer or film 3 is delimited by an outer edge 3c.

The anti-adhesion material forming the first barrier layer or film 3 allows preventing post surgical adhesions between the viscera organs of the abdominal cavity and the porous material forming the reinforcement layer 2. The first surface of the first barrier layer, such as the film 3, covers at least a central part of the area of the second surface 2b of the reinforcement layer 2. In the example shown on FIGS. 1-3, the first surface of the first barrier layer, such as the film 3, covers the entire area of the second surface 2b of the reinforcement layer 2. As such, the second surface of the first barrier layer, such as the film 3, is intended to face the abdominal cavity and therefore protects the viscera organs of the abdominal cavity from the reinforcement layer 2.

In other embodiments (see FIG. 7B), the first surface of the first barrier layer, such as the film 3, covers only a central part of the area of the second surface 2b of the reinforcement layer 2.

The anti-adhesion material may be chosen from among bioresorbable materials, non-bioresorbable materials and mixtures thereof. The non-bioresorbable anti-adhesion materials can be selected from among polytetrafluoroethylene, polyethylene glycols, polysiloxanes, polyurethanes, and mixtures thereof.

The anti-adhesion material is preferably bioresorbable: the bioresorbable materials suitable for said anti-adhesion material can be selected from among collagens, oxidized celluloses, polyethylene glycol, polyacrylates, trimethylene carbonates, caprolactones, dioxanones, butyric or glycolic acid, lactic acid, glycolides, lactides, polysaccharides, for example chitosans, polyglucuronic acids, hyaluronic acids, dextrans, and mixtures thereof.

For example, the film 3 of FIGS. 1-3 is a film of a copolymer of glycolide, lactide, trimethylene carbonate and e-caprolactone, the preparation of which is described in U.S. Pat. No. 6,235,869. The film may be applied on the reinforcement layer 2 by a lamination process.

In other embodiments, the film 3 may be a non porous collagen film or a bioabsorbable collagen film based on oxidized collagen with polyethylene glycol. Such films based on collagen may be obtained by application on the second surface of the reinforcement layer of a solution based on collagen and by gelification of the solution thereon.

In other embodiments, the first barrier layer is a coating obtained by spraying a solution or a suspension of an anti-adhesion material on the second surface of the reinforcement layer 2.

The prosthesis 1 further comprises a second barrier layer, consisting in a flap member under the form of a first skirt 4 on FIGS. 1-3, made of a biocompatible anti-adhesion material. The first skirt 4 is a piece of sheet of biocompatible anti-adhesion material under the form of an annular band shaped film. The anti-adhesion material forming the second barrier layer or first skirt 4 allows preventing post surgical adhesions between the viscera organs of the abdominal cavity and the fixing means used to fix the prosthesis to the abdominal wall, as will appear from the description below.

The anti-adhesion material forming the second barrier layer, namely the first skirt 4, may be chosen among the same materials as described above for the anti-adhesion material forming the first barrier layer. The anti-adhesion material forming the first skirt 4 may be identical or different than the anti-adhesion material forming the film 3.

For example, the first skirt 4 is made of a film of a copolymer of glycolide, lactide, trimethylene carbonate and e-caprolactone, the preparation of which is described in U.S. Pat. No. 6,235,869.

The first skirt 4 has an outer edge 5a and an inner edge 5b. The annular band forming the first skirt 4 has preferably a width, corresponding to the length measured along a direction aligned on a radius of the reinforcement layer extending from the center C of the reinforcement layer to a point of the outer edge of the reinforcement layer, ranging from about 1 cm to 4 cm, preferably from 2 cm to 3 cm. The first skirt 4 is therefore particularly adapted for covering the proximal ends of the fixing means used for fixing the prosthesis 1 to the abdominal wall.

Figure 10:
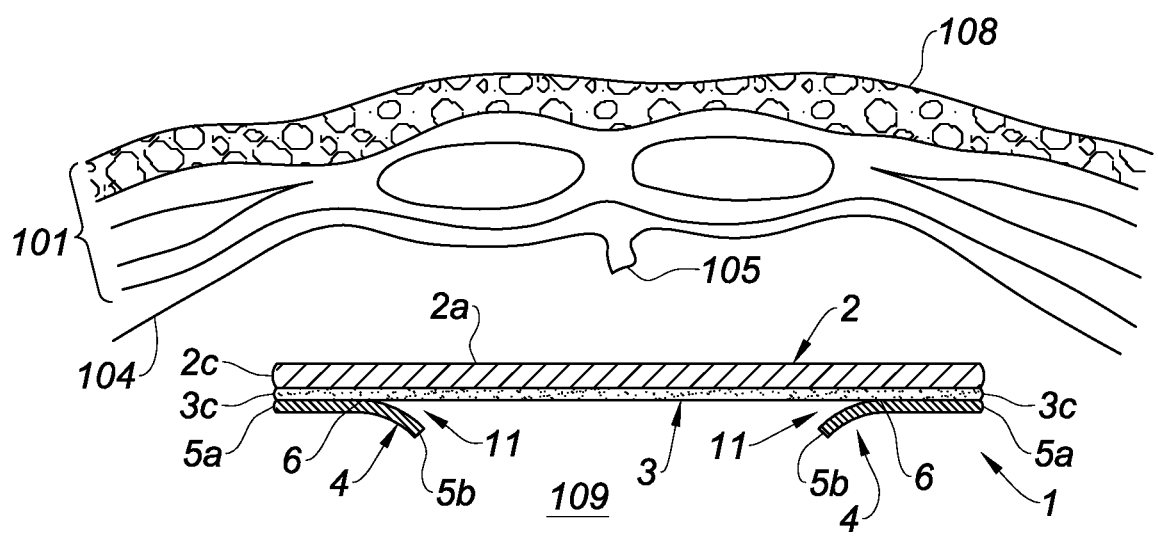
FIG. 10 is a sectional view of the hernia of FIG. 9 once the hernia sac (not shown) has been reduced and the prosthesis of FIG. 1 has been introduced in the abdominal cavity.
Figure 11:
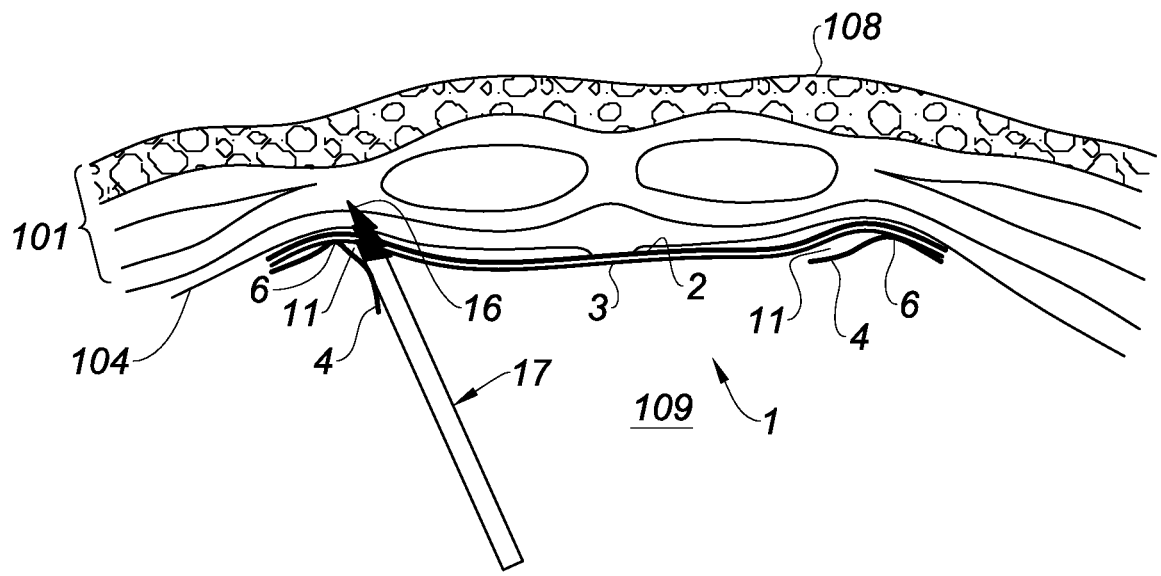
FIG. 11 is a cross sectional view showing the tacking of the prosthesis of FIG. 1 to the abdominal wall.
Figure 12:
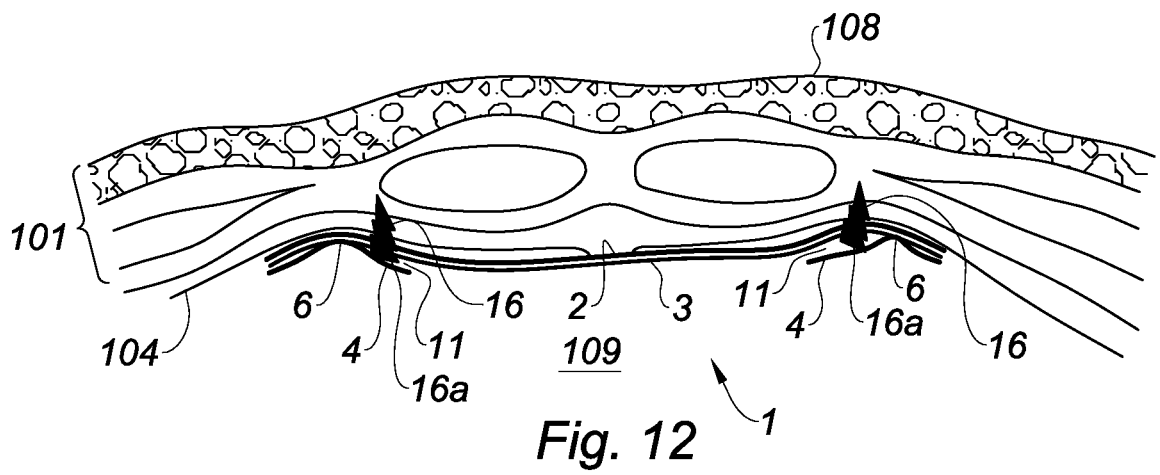
FIG. 12 is a cross sectional view showing the prosthesis of FIG. 1 fixed to the abdominal wall, with the first barrier layer of the prosthesis covering the heads of the tacks.

The first skirt 4 further shows a first surface 4a, intended to face the first barrier layer or film 3, and a second surface 4b intended to face the abdominal cavity (see FIGS. 10-12). In embodiments (not shown), the first skirt 4 is provided on its surface regarding the film 3 with a tacky layer of biocompatible materials capable of sticking to film 3. The biocompatible materials suitable for forming the tacky layer may be selected from collagen-based, polylactone-based, polylactic, polyethylene glycol, polysaccharides and/or polyvinyl alcohol based surgical adhesives, fibrin glues, and combinations thereof.

In the example shown, with reference to FIG. 3, the outer edge 5a of the first skirt 4 is attached to the second surface of the reinforcement layer 2 along the outer edge 2c of the reinforcement layer 2 by the intermediate of the film 3. In other words, the outer edge 5a of the first skirt 4 is therefore attached along the outer edge 3c of the film 3. The inner edge 5b of the first skirt 4 is left free.

Preferably, the outer edge 5a of the first skirt 4 is attached along the outer edge 3c of the film 3 in a continuous way. For example, the outer edge 5a of the first skirt 4 is attached to the film 3 so as to define an attaching line 6 which is offset towards a center of the prosthesis from about 0.5 to about 2 cm, preferably about 1 cm, from said outer edge. As will appear from the description of FIGS. 10-12 below, such embodiments guaranty that the fixing means, such as clips, tacks, screws, spirals, straps, staples, suture or transfacial sutures, will not move too close to the outer edge of the prosthesis 1.

The first barrier layer, such as the film 3, and the second barrier layer, such as the first skirt 4, may be attached one to the other by attaching means selected from the group comprising ultrasonic welding, hot compression welding, gluing and combinations thereof.

For example, in case the anti-adhesion material forming the first and second barrier layers is selected from polylactic acid, polyglycolic acid, trimethylene carbonates, polyethylene glycol, polycaprolactone, and combinations thereof, the first barrier layer and the second barrier layer may be attached one to the other via ultrasonic welding by applying pressure and piezo energy to ensure local fusion of the two barriers.

Alternatively, in case the anti-adhesion material forming the first and second barrier layers is a collagen or derivatives thereof, the first barrier layer and the second barrier layer may be attached one to the other via a gluing agent, for example a gluing agent capable of locally solubilising both barriers in order to fusion them. The gluing agent may be a collagen water solution, with or without a crosslinking agent. For example, in contact with such a collagen water solution, the first and second barriers' surfaces will tend to melt, and by a drying process the first and second barriers will be unified.

For example, in the present example, the film 3 and the first skirt 4 being each made of a film of a copolymer of glycolide, lactide, trimethylene carbonate and e-caprolactone, the first skirt 4 is attached to the film 3 by ultrasonic welding. The first skirt 4 is therefore securely attached to the film 3.

As shown on FIG. 3 and as will appear from the description below, the shape of the flap member forming the second barrier layer, namely the first skirt 4, and the way it is attached to the first barrier layer, eg the film 3, allow creating an adequate protected space 11 located between the film 3 and the first skirt 4 for lodging the fixing means, such as tacks, intended to fix the prosthesis to the abdominal wall (see FIG. 12).

With reference to FIGS. 4-8 are shown other embodiments of the prosthesis 1 of the invention. In these Figures, references designating the same elements as in the prosthesis 1 of FIGS. 1-3 have been maintained.

Figure 4:
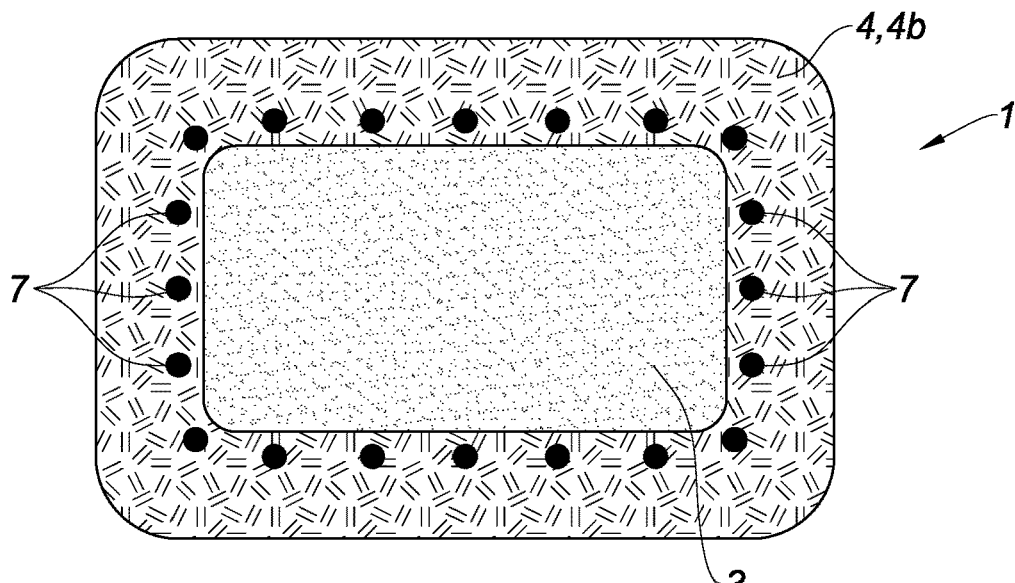
FIG. 4 is a bottom view of another embodiment of the prosthesis of the invention.

With reference to FIG. 4 is shown an alternative embodiment of a prosthesis 1 of the invention, provided with markings 7 intended to indicate to the surgeon where to locate one or more fixing means for fixing the prosthesis 1 to the abdominal wall. On the example shown, the markings 7 are regularly spaced from one another along a perimeter of the second barrier layer or first skirt 4. With reference to FIG. 4, the markings 7 are under the form of colored spots located on the surface 4b of the first skirt 4 which is intended to face the abdominal cavity: the fixing means are optimally positioned underneath the first skirt 4, at points corresponding to the localization of the colored spots. In other embodiments not shown, the markings may have the shape of crosses, triangles, etc . . .

In embodiments, the markings are distant 1.5 cm from one another. Such embodiments allow the surgeon to easily position the fixing means, such as tacks, at intervals of 1.5 cm. Such a fixation technique is usually associated with a low recurrence rate of the hernia.

Alternatively, markings, such as a dotted line, may be provided on the reinforcement layer 2 itself.

In embodiments, the second barrier layer or first skirt 4 may be provided with identification means for distinguishing said first skirt 4 from said first barrier layer or film 3. For example, the first skirt 4 may show a color different than that of the film 3. In other embodiments, the first skirt 4 may be provided with specific designs drawn on flap member(s), such as geometric figures, etc . . .

Figure 5:
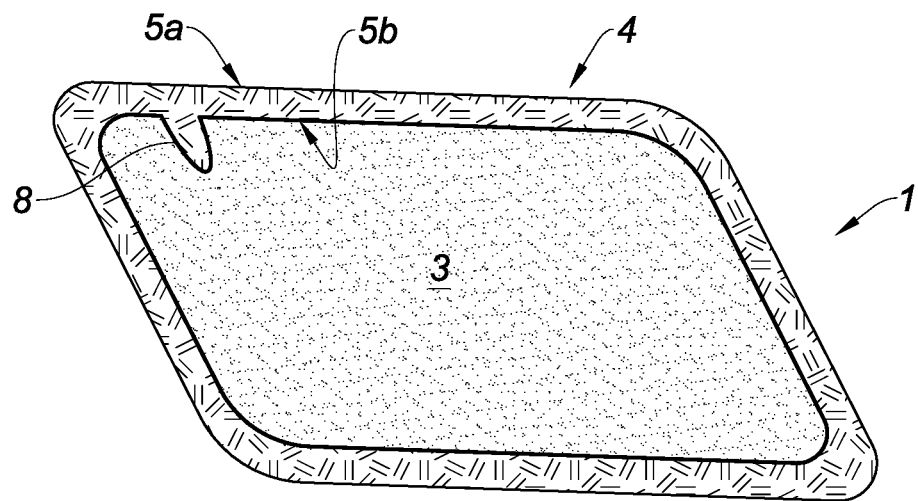
FIG. 5 is a bottom view of another embodiment of the prosthesis of the invention.

With reference to FIG. 5 is shown an alternative embodiment of a prosthesis 1 of the invention, wherein the inner edge 5b of the second barrier layer or first skirt 4, is provided with a projecting tab 8. The projecting tab 8 is intended to help the surgeon lift the first skirt 4 from the film 3. In particular, the surgeon may grasp the projecting tab 8 with a grasper or other instrument so as to pull on it and lift the inner edge 5b of the first skirt 4, thereby opening a larger access to the protected space located between the first skirt 4 and the film 3.

In embodiments not shown, the first skirt 4 could be provided with one or more tabs, positioned anywhere along the length of its inner edge, for example positioned along the mid-line of a side of the inner edge where a minimal amount of force will create a greater separation between the first skirt 4 and the reinforcement layer 2 along that side of the first skirt 4.

Figure 6:
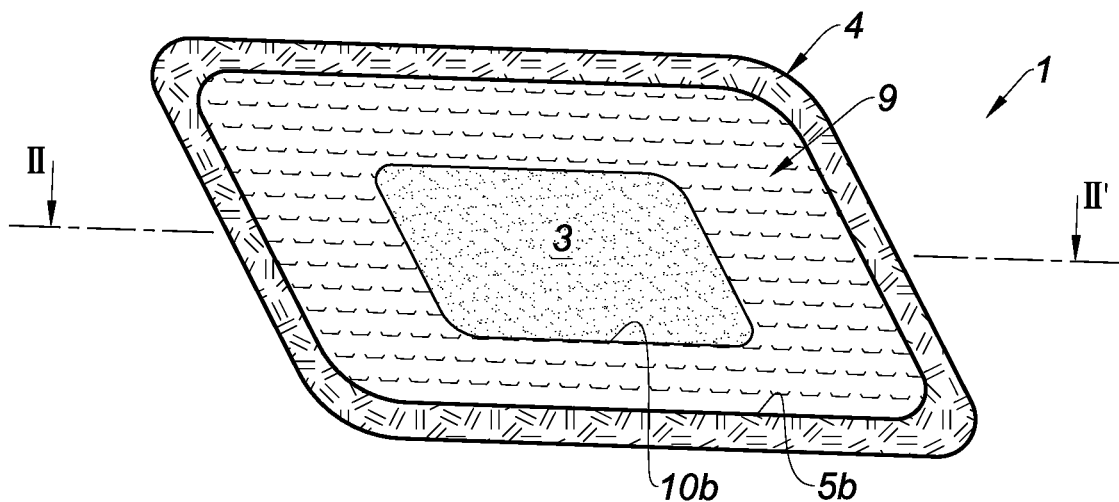
FIG. 6 is a bottom view of another embodiment of the prosthesis of the invention.
Figure 7A:
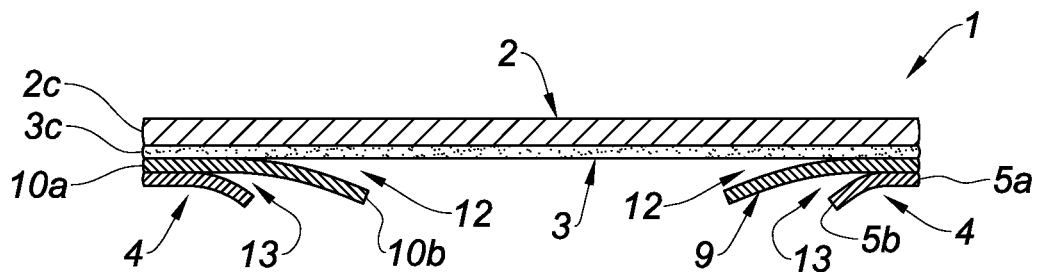
FIG. 7A is a cross section view of the prosthesis of FIG. 6 taken along plane II-II'.

With reference to FIGS. 6 and 7A, is shown an alternative embodiment of a prosthesis 1 of the invention, wherein the second barrier layer comprises a first flap member, under the form of a first skirt 4 like in FIGS. 1-3, and a second flap member, under the form of a second skirt 9. In the example shown, the second barrier layer consists in said first and second skirts (4, 9). The second skirt 9 is a piece of sheet of biocompatible anti-adhesion material under the form of an annular band shaped film. The anti-adhesion material used for the second skirt 9 may be the same or different than the anti-adhesion material used for the first skirt 4.

For example, the second skirt 9 is made of a film of a copolymer of glycolide, lactide, trimethylene carbonate and e-caprolactone, the preparation of which is described in U.S. Pat. No. 6,235,869.

In the Example shown on FIGS. 6 and 7A, the second skirt 9 is located between the first barrier layer or film 3 and the first flap member or first skirt 4. The second skirt 9 is delimited by an outer edge 10a and an inner edge 10b. The outer edge 10a of the second skirt 9 is substantially attached along the outer edge 2c of the reinforcement layer 2 by the intermediate of the outer edge 3c of the film 3 forming the first barrier layer.

Moreover, as shown on FIGS. 6 and 7A, the inner edge 10b of the second skirt 9 is free and extends beyond the inner edge 5b of the annular band film 4 in the direction of the center C (see FIG. 1) of the reinforcement layer 2.

The second skirt 9 may be attached to the film 3 and to the first skirt 4 by the same methods as described above for attaching the film 3 to the first skirt 4. For example, in the present example, the film 3, the second skirt 9 and the first skirt 4 being each made of a film of a copolymer of glycolide, lactide, trimethylene carbonate and e-caprolactone, the first skirt 4, second skirt 9 and film 3 may be attached altogether by ultrasonic welding. The first skirt 4, second skirt and film 3 are therefore securely attached together.

As shown on FIG. 7A, the respective shapes and attachment structures of the first skirt 4 and of the second skirt 9 allow creating two different protected spaces (12, 13) for lodging fixing means, such as tacks, intended to fix the prosthesis to the abdominal wall. With reference to FIG. 7A, a first protected space 12 is created between the film 3 and the second skirt 9, and a second protected space 13 is created between the second skirt 9 and the first skirt 4.

Figure 7B:
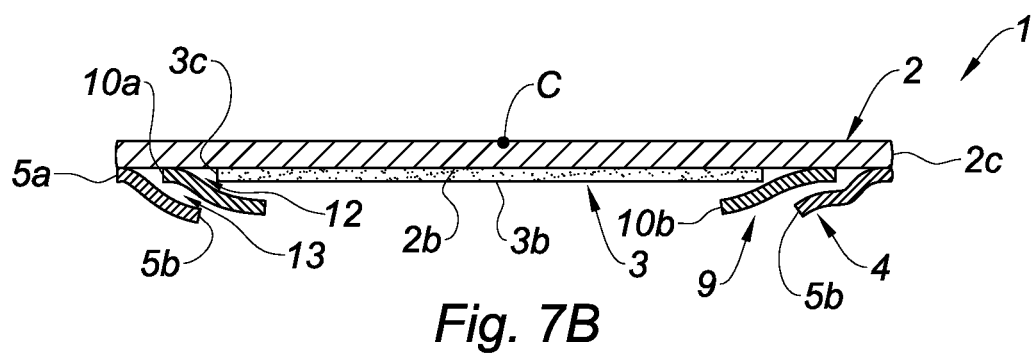
FIG. 7B is a cross section view of an alternative embodiment of the prosthesis of FIG. 6.

With reference to FIG. 7B, is shown an alternative embodiment of a prosthesis 1 of FIG. 7A in which the first barrier layer under the form of the film 3 covers only a central part of the area of the second surface of the reinforcement layer 2 and the outer edge 10a of the second skirt 9 is substantially attached to the second surface of the reinforcement layer 2 along a line located between the outer edge 2c of the reinforcement layer 2 and the outer edge 3c of the first barrier layer or film 3. In particular, the first skirt 4 and the second skirt 9 are concentrically positioned one with respect to the other, so that the outer edge 10a of the second skirt 9 is substantially attached to the second surface of the reinforcement layer 2 along a line substantially parallel to the outer edge 2c of the reinforcement layer 2, the line being located between the outer edge 2c of the reinforcement layer 2 and the outer edge 3c of the first barrier layer formed by the film 3.

As appears from FIG. 7B, the second barrier layer, which consists in the first skirt 4 and the second skirt 9, is shaped and dimensioned so as to cover at least the part of the area of the second surface of the reinforcement layer 2 that is not covered by the first barrier layer or film 3. In particular, in the example shown, the inner edge 5b of the first skirt 4 forming the first flap member overlaps the outer edge 10a of the second skirt 9 forming the second flap member, and the inner edge 10b of the second skirt 9 overlaps the outer edge 3c of the film 3 forming the first barrier layer. As a result, the entire area of the second surface of the reinforcement layer 2 is safely covered by anti-adhesion material, said anti-adhesion material being provided either by the film 3 forming the first barrier layer or by the first skirt 4 or the second skirt 9 forming the first and second flap members of the second barrier layer. Such an embodiment allows reducing the amount of anti-adhesion material implanted into the body of the patient, while ensuring a safe covering of the entire area of the second surface of the reinforcement layer 2 by an anti-adhesion material. Moreover, when the anti-adhesion materials forming the first barrier layer and the second barrier layer are biodegradable, such embodiments allow an even degradation profile for the first and second barrier layers across the entire second surface of the reinforcement layer 2.

Such embodiments of the prosthesis 1 of the invention as shown on FIGS. 7A and 7B are particularly useful for allowing the surgeon to complete a reinforced fixation. Indeed, when the hernia defect to be repaired is large, it may be useful to fix the prosthesis 1 to the abdominal wall using two sets of fixing means. For example, a first set of tacks may be positioned according to a circle configuration in the vicinity of the edges of the defect. In the present example, this first circle of tacks could be positioned in the first protected space 12 of prosthesis 1 of FIGS. 6-7B, with for example a regular space between two adjacent tacks, such as 1 cm. Then, a second set of tacks may be positioned according to a second circle, of larger diameter, in the vicinity of the peripheral outer edge of the prosthesis, preferably at a distance of about 1 cm set back from this peripheral outer edge, as explained above. In the present example, this second circle of tacks could be positioned in the second protected space 13 of prosthesis 1 of FIGS. 6-7B, with for example a regular space between two adjacent tacks, such as 1 cm. Once the prosthesis 1 is fixed to the abdominal wall, the second skirt 9 covers the heads of the tacks positioned on the first circle, and the first skirt 4 covers the tacks of the second circle. The viscera organs of the abdominal cavity are therefore well protected from the fixing means, such as tacks, of the prosthesis, and potential surgical adhesion between the tacks and the viscera organs are avoided.

Figure 8:
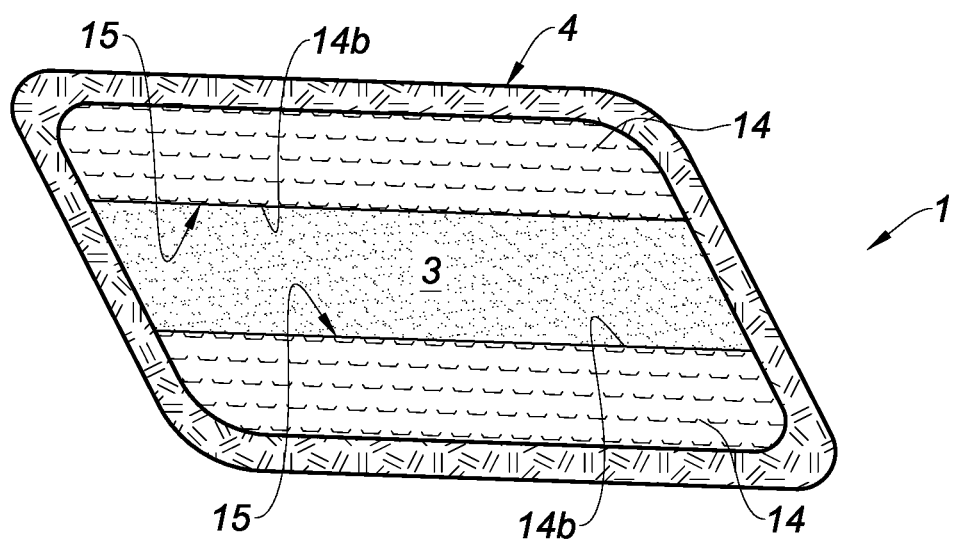
FIG. 8 is a bottom view of another embodiment of the prosthesis of the invention.

With reference to FIG. 8 is shown an alternative embodiment of a prosthesis 1 of the invention, in which the second barrier layer comprises a first flap member, under the form of a first skirt 4 like in FIGS. 1-3, and a second and third flap members, the second and third flap members each being under the form of a longitudinal tape portion 14 intended to be positioned in regards of edges of the hernia defect once the prosthesis 1 is implanted. In the example shown, the second barrier layer consists in the first skirt 4 and the two longitudinal tape portions 14. The two longitudinal tape portions 14 extend from a small side of the prosthesis 1 to the other. The outer edge (not visible) of each longitudinal tape portion 14 is attached to the reinforcement layer by the intermediate of the film 3, the inner edge 14b of each longitudinal tape 14 being left free.

Such embodiment allows creating two longitudinal protected spaces 15, located between the film 3 and the tape portions 14, for lodging fixing means, such as tacks, in the vicinity of the defect edges.

The method of treating a hernia defect with the prosthesis 1 of FIGS. 1-3 will now be described in reference to FIGS. 9-12. In FIGS. 11 and 12, the prosthesis of FIGS. 1-3 is drawn in a simplified manner so as to clarify the Figures.

Figure 9:
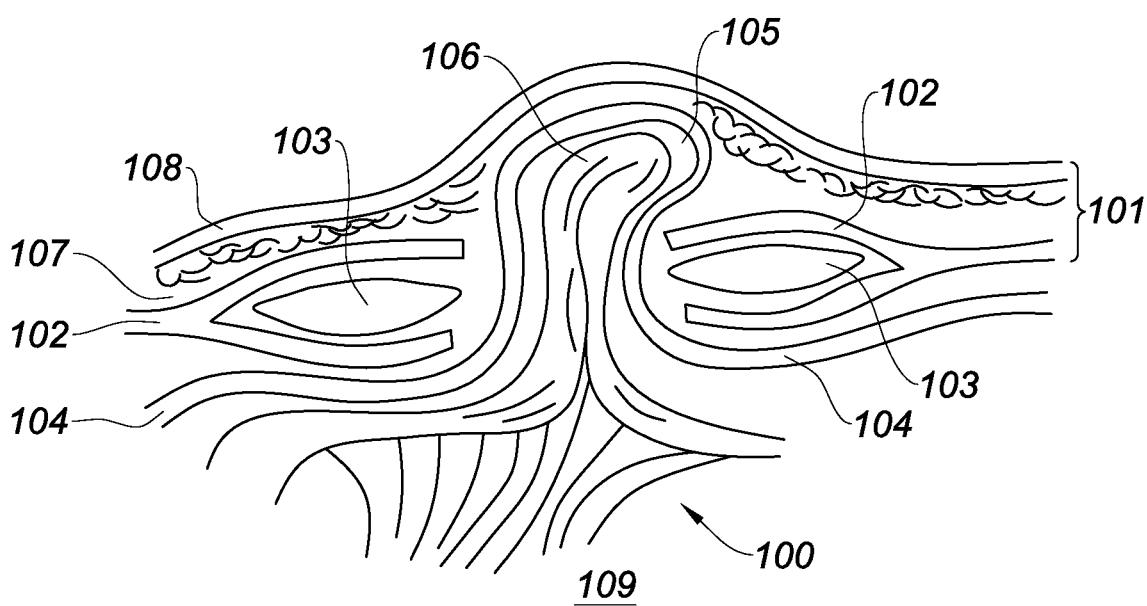
FIG. 9 is a sectional view of a median abdominal hernia.

FIG. 9 shows a hernia defect 100 of the abdominal wall 101, characterized by a break in continuity of the fascia 102 surrounding the rectus muscles 103 and by a passage through the peritoneum 104 forming a sac, the hernial sac 105, which contains either fat (greater omentum) or part of the viscera 106, and which thus exerts pressure on the fatty tissues 107 and lies flush with the skin 108. Treatment of a hernia defect 100 involves repositioning and maintaining the viscera 106 in the abdominal cavity 109.

FIG. 10 shows the hernia defect from FIG. 9 after insufflation of the abdominal cavity 109 and reduction of the hernial sac 105 by the surgeon by laparoscopic surgery. The viscera organs are not shown in FIG. 10: they have been pushed back towards the abdominal cavity 109. Once the hernial sac 105 is reduced, the prosthesis 1 of FIGS. 1-3 is introduced in the abdominal cavity 109 by means of a trocar (not shown) and positioned with the first surface 2a of the reinforcement layer 2 facing the abdominal wall 101 and peritoneum 104, as shown on FIG. 10.

The surgeon then moves the prosthesis 1 closer to the peritoneum 104/abdominal wall 101 so that the first surface 2a of the prosthesis 1 bears on the peritoneum 104/abdominal wall 101; the surgeon grasps the inner perimeter 5b of the first skirt 4 with a laparoscopic tool so as to lift the first skirt 4 and gain access to the protected space 11. A tacker 17 is then introduced in the abdominal cavity 109 by means of a trocar (not shown). The distal end of the tacker 17 is introduced in the protected space 11 and a tack 16 is fired in the direction of the peritoneum 104/abdominal wall 101, as shown on FIG. 11.

In embodiments where the attaching line 6 of the prosthesis 1 is continuous and offset towards the center of the prosthesis 1 from the outer edge 3c of the first barrier layer of film 3, as shown on FIGS. 3, 11 and 12, the surgeon may feel particularly comfortable with the gesture of introducing the distal end of the tacker 17 into the protected space 11 and of firing a tack 16, as he is ensured that the tacks 16 will not move too close to the outer edge of the prosthesis 1. In addition, because of the strong and efficient attaching between the second barrier layer or first skirt 4 and the reinforcement layer 2 or first barrier layer or film 3, the surgeon knows that he can firmly push on the tacker 17 in the distal direction and therefore in the direction of the abdominal wall without fearing that the second barrier layer separates from the first barrier layer and/or from the reinforcement layer. The integrity of the assembly of the reinforcement layer/first barrier layer and second barrier layer is not compromised by the movement of the tacker 17 in the protected space 11.

The same operation is repeated for each tack 16, as many times as deemed necessary by the surgeon in order to obtain an efficient fixation of the prosthesis 1 to the peritoneum 104/abdominal wall 101.

With reference to FIG. 12, two tacks 16 are shown after they have been fired in the protected space 11. As shown on this Figure, the tacks 16 fix both the reinforcement layer 2 and the first barrier layer of film 3 to the peritoneum 104/abdominal wall 101 with their proximal end, namely their head 16a, protruding in the protected space 11. The first skirt 4 covers the heads 16a of the tacks 16 so that no part of the tacks 16 is in contact with the viscera organs (not shown) present in the abdominal cavity 109.

As a result, the risk of recurrence provoked by the formation of post-surgical adhesions between the fixing means, such as tacks 16, and the viscera organs of the abdominal cavity 109 is dramatically decreased with the prosthesis 1 of the invention.

In embodiments, the first skirt 4 is provided on its surface regarding the film 3 with a tacky layer of biocompatible materials, and the surgeon may cover the head 16a of each tack 16 and then stick the first skirt 4 to the film 3 for a reinforced protection and reliable separation of the tack's head from the surrounding biological issues of the abdominal cavity.

The prosthesis of the invention therefore allows completing intraperitoneal repair with fewer risks of recurrence or of postoperative complications.

The invention claimed is:

1. A prosthesis for treating a hernia defect in an abdominal wall comprising:
   at least one reinforcement layer comprising a biocompatible porous material, said at least one reinforcement layer including a first surface intended to face the abdominal wall and a second surface opposite said first surface, said at least one reinforcement layer being delimited by an outer edge,
at least one first barrier layer comprising a biocompatible anti-adhesion material, said at least one first barrier layer including a first surface and a second surface opposite said first surface of the at least one first barrier layer, the first surface of the at least one first barrier layer covering substantially a central part of an area of the second surface of said at least one reinforcement layer, the second surface of said at least one first barrier layer being intended to face the abdominal cavity, said at least one first barrier layer being delimited by an outer edge,
at least one second barrier layer, said at least one second barrier layer being shaped and dimensioned so as to cover at least a part of a remaining area of the second surface of said at least one reinforcement layer that is not covered by the at least one first barrier layer, said at least one second barrier layer comprising one or more flap members, each of the one or more flap members being formed of a piece of sheet of biocompatible anti-adhesion material, and having at least an outer edge attached to the second surface of the at least one reinforcement layer and a free inner edge, wherein the outer edge of the one or more flap members is spaced from the outer edge of the at least one first barrier layer with at least one protected space on the at least one reinforcement layer positioned therebetween.

2. The prosthesis of claim 1, wherein the one or more flap members include at least a first flap member having a form of an annular band, an outer edge of said first flap member being substantially attached to the second surface of the at least one reinforcement layer along the outer edge of said at least one reinforcement layer.

3. The prosthesis of claim 2, wherein the one or more flap members further comprises at least a second flap member, an outer edge of said second flap member being substantially attached to the second surface of the at least one reinforcement layer along a line located between the outer edge of the at least one reinforcement layer and the outer edge of the at least one first barrier layer.

4. The prosthesis of claim 3, wherein said second flap member has a form of a second annular band, said first and second flap members being concentrically positioned one with respect to the other, so that the outer edge of said second flap member is substantially attached to the second surface of the at least one reinforcement layer along a line substantially parallel to the outer edge of the reinforcement layer, said line being located between the outer edge of the at least one reinforcement layer and the outer edge of the at least one first barrier layer.

5. The prosthesis of claim 3, wherein the one or more flap members further comprises a third flap member having an outer edge, each of said second and third flap member having a form of a tape portion, the respective outer edges of said second and third flap members being substantially attached to the second surface of the at least one reinforcement layer along line(s) located between the outer edge of the at least one reinforcement layer and the outer edge of the at least one first barrier layer, said line(s) being intended to be positioned in regards of a vicinity of edges of the hernia defect.

6. The prosthesis of claim 2, wherein the outer edge of the first flap member is spaced from the outer edge of the second flap member with a first protected space on the at least one reinforcement layer positioned therebetween and the outer edge of the second flap member is spaced from the outer edge of the at least one first barrier layer with a second protected space on the at least one reinforcement layer positioned therebetween.

7. The prosthesis of claim 2, wherein said at least one second barrier layer consists in said first flap member.

8. The prosthesis of claim 2, wherein the outer edge of said first flap member is attached along the outer edge of said at least one reinforcement layer in a continuous way.

9. The prosthesis of claim 2, wherein the outer edge of said first flap member is attached to the second surface of the at least one reinforcement layer so as to define an attaching line which is offset towards a center of the prosthesis from about 0.5 to about 2 cm from the outer edge of said at least one reinforcement layer.

10. The prosthesis of claim 2, wherein the outer edge of said first flap member is attached to the second surface of the at least one reinforcement layer so as to define an attaching line which is offset towards a center of the prosthesis from about 1 cm from the outer edge of said at least one reinforcement layer.

11. The prosthesis of claim 1, wherein the outer edge of said one or more flap members is attached to the second surface of the at least one reinforcement layer by attaching means selected from the group comprising ultrasonic welding, hot compression welding, gluing and combinations thereof.

12. The prosthesis of claim 1, wherein the addition of each area of the one or more flap members amounts altogether to a total area of the one or more flap members which is less than 120% of the remaining area of the second surface of said at least one reinforcement layer that is not covered by the first barrier layer.

13. The prosthesis of claim 1, wherein said at least one second barrier layer is provided with markings intended to indicate to a surgeon where to locate one or more fixing means for fixing the prosthesis to the abdominal wall.

14. The prosthesis according to claim 13, wherein said markings are colored spots located on a surface of said at least one second barrier layer intended to face the abdominal cavity.

15. The prosthesis according to claim 14, wherein said markings are regularly spaced from one another along a perimeter of said at least one second barrier layer.

16. The prosthesis of claim 1, wherein the free inner edge of said one or more flap members is provided with one or more projecting tabs intended to help a surgeon lift said one or more flap members from said at least one reinforcement layer.

17. The prosthesis of claim 1, wherein a smallest dimension of a shape of the piece of sheet of anti-adhesion material forming the one or more flap members ranges from about 1 cm to 4 cm.

18. The prosthesis of claim 17, wherein the smallest dimension of the shape of the piece of sheet of anti-adhesion material forming the one or more flap members ranges from about 2 cm to 3 cm.

19. The prosthesis of claim 1, wherein the one or more flap members forming the at least one second barrier layer provided on a surface facing the at least one reinforcement layer or the at least one first barrier layer with a tacky layer of biocompatible materials capable of sticking to said at least one reinforcement layer or at least one first barrier layer.

20. The prosthesis of claim 1, wherein the free inner edge overlaps the outer edge of the at least one first barrier layer.

21. The prosthesis of claim 3, wherein the at least one protected space includes at least a first protected space and a second protected space, and wherein the outer edge of the first flap member is spaced from the outer edge of the second flap member with the first protected space on the at least one reinforcement layer positioned therebetween, and the outer edge of the second flap member is spaced from the outer edge of the at least one first barrier layer with the second protected space on the at least one reinforcement layer positioned therebetween.

\* \* \* \* \*